(12) United States Patent
Beaty, Jr. et al.

(10) Patent No.: US 10,119,931 B2
(45) Date of Patent: Nov. 6, 2018

(54) METHODS OF ELECTROCHEMICALLY MEASURING AN ANALYTE WITH A TEST SEQUENCE HAVING A PULSED DC BLOCK AS WELL AS DEVICES, APPARATUSES AND SYSTEMS INCORPORATING THE SAME

(71) Applicant: Roche Diabetes Care, Inc., Indianapolis, IN (US)

(72) Inventors: Terry A. Beaty, Jr., Indianapolis, IN (US); Scott E. Carpenter, Pendleton, IN (US); Zheng Zheng Pan, Plano, TX (US); Nigel A. Surridge, Indianapolis, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 516 days.

(21) Appl. No.: 14/851,621

(22) Filed: Sep. 11, 2015

(65) Prior Publication Data
US 2016/0003764 A1    Jan. 7, 2016

Related U.S. Application Data

(63) Continuation of application No. PCT/EP2014/054965, filed on Mar. 13, 2014.

(60) Provisional application No. 61/792,748, filed on Mar. 15, 2013, provisional application No. 61/801,826, filed on Mar. 15, 2013.

(51) Int. Cl.
*G01N 27/327* (2006.01)

(52) U.S. Cl.
CPC .............. *G01N 27/3274* (2013.01)

(58) Field of Classification Search
CPC ...................... G01N 27/327–27/3274
See application file for complete search history.

(56) References Cited

U.S. PATENT DOCUMENTS

| | | |
|---|---|---|
| 2003/0060692 A1 | 3/2003 | Ruchti et al. |
| 2004/0157339 A1 | 8/2004 | Burke et al. |

(Continued)

FOREIGN PATENT DOCUMENTS

| | | |
|---|---|---|
| EP | 1156324 A1 | 11/2001 |
| EP | 1467206 A1 | 10/2004 |

(Continued)

OTHER PUBLICATIONS

Gunasingham; et al., "Pulsed amperometric detection of glucose using a mediated enzyme electrode", Journal of Electroanalytical Chemistry and Interfacial Electrochemistry, Jul. 25, 1990, vol. 287, No. 2, pp. 349-362.

*Primary Examiner* — J. Christopher Ball

(57) ABSTRACT

Methods are disclosed for measuring an analyte concentration in a fluidic sample. Such methods further allow one to correct and/or compensate for confounding variables such as hematocrit (Hct), temperature or both before providing an analyte concentration. The measurement methods utilize information obtained from test sequences having at least one AC block and at least one pulsed DC block, where pulsed DC block includes at least one recovery potential, and where a closed circuit condition of the electrode system is maintained during the DC block. Also disclosed are devices, apparatuses and systems incorporating the various measurement methods.

21 Claims, 15 Drawing Sheets

(56) References Cited

U.S. PATENT DOCUMENTS

| | | |
|---|---|---|
| 2005/0279631 A1 | 12/2005 | Celentano |
| 2007/0102292 A1 | 5/2007 | Dreibholz et al. |
| 2008/0099347 A1* | 5/2008 | Barlag ............... G01N 27/3277 205/793.5 |
| 2009/0030641 A1 | 1/2009 | Fjield et al. |
| 2011/0162978 A1 | 7/2011 | Cardosi et al. |
| 2014/0027312 A1 | 1/2014 | MacFie et al. |

FOREIGN PATENT DOCUMENTS

| | | |
|---|---|---|
| EP | 2042865 A2 | 4/2009 |
| EP | 2138841 A2 | 12/2009 |
| EP | 2261646 B1 | 7/2015 |
| JP | 2002-514452 A | 5/2002 |
| JP | 2006-522923 A | 10/2006 |
| JP | 2007-147638 A | 6/2007 |
| JP | 2007-524825 A | 8/2007 |
| JP | 2009-524605 A | 7/2009 |
| JP | 2010-507808 A | 3/2010 |
| JP | 2015-530582 A | 10/2015 |
| WO | 1999032881 A1 | 7/1999 |
| WO | 2001021827 A1 | 3/2001 |
| WO | 2003060154 A2 | 7/2003 |
| WO | 2006109279 A2 | 10/2006 |
| WO | 2007100651 A1 | 9/2007 |
| WO | 2008036516 A1 | 3/2008 |
| WO | 2009075951 A1 | 6/2009 |
| WO | WO2012084194 A1 | 6/2012 |
| WO | 2012134890 A1 | 10/2012 |

\* cited by examiner

METHODS OF ELECTROCHEMICALLY MEASURING AN ANALYTE WITH A TEST SEQUENCE HAVING A PULSED DC BLOCK AS WELL AS DEVICES, APPARATUSES AND SYSTEMS INCORPORATING THE SAME

CROSS-REFERENCE TO RELATED APPLICATIONS

This patent application is a continuation of Int'l Patent Application No. PCT/EP2014/054965 (filed 13 Mar. 2014), which claims priority to and the benefit of U.S. Provisional Patent Application Nos. 61/792,748 and 61/801,826 (filed 15 Mar. 2013). Each patent application is incorporated herein by reference as if set forth in its entirety.

TECHNICAL FIELD

The disclosure relates generally to mathematics and medicine, and more particularly, it relates to methods of electrochemically measuring an analyte in a fluidic sample based upon response currents obtained from an electrical test sequence having at least one pulsed direct current (DC) block.

BACKGROUND

Significant benefits can be realized from electrochemically measuring analytes in fluidic samples (i.e., biological or environmental). For example, individuals with diabetes can benefit from measuring glucose. Those potentially at-risk for heart disease can benefit from measuring cholesterols and triglycerides among other analytes. These are but a few examples of the benefits of measuring analytes in biological samples. Advancements in the medical sciences are identifying a growing number of analytes that can be electrochemically analyzed in a fluidic sample.

The accuracy of present approaches to electrochemically measuring analytes such as glucose can be negatively affected by a number of confounding variables including variations in reagent thickness, wetting of the reagent, rate of sample diffusion, hematocrit (Hct), temperature, salt and other confounding variables. These confounding variables can cause an increase or decrease in an observed magnitude of, for example, a current response that is proportional to glucose, thereby causing a deviation from the "true" glucose concentration.

A number of approaches are known for correcting errors attributable to variation in test sample and biosensor characteristics. Some approaches seek to perform active correction on analyte measurements. For example, US Patent Application Publication No. 2009/0236237 discloses biosensor measurement systems including temperature correction algorithms for correcting analyte measurements based upon measurements of the ambient temperature, the temperature of the biosensor itself, or the time between when a biosensor is attached to a measurement device and a sample is provided to the biosensor. In another example, U.S. Pat. No. 7,407,811 discloses a system and method for measuring blood glucose that corrects for variation in temperature, Hct and other confounding variables by measuring impedance of a blood sample to an AC excitation and using the impedance (or impedance derived admittance and phase information) to correct for the effects of such interferents.

Other approaches seek to control the physical characteristics of biosensors. For example, U.S. Pat. No. 7,749,437 discloses methods for controlling reagent thickness and uniformity.

There also have been attempts to perform electrochemical analyte measurements using pulsed signals. For example, Barker et al. disclose that an alternating polarographic square wave potential can be applied to a test cell and that the amplitude of the AC current response was measured just before each change of applied voltage to detect concentrations of metallic ions. See, Barker et al. (1952) *Int'l Congr. Anal. Chem.* 77:685-696. Barker et al. also disclose that their method ameliorates the undesirable effect of the rate of double-layer capacitance current on the sensitivity of an A/C polarograph.

In addition, Gunasingham et al. disclose a pulsed amperometric detection method for a mediator-based enzyme electrode that applies a potential pulse signal to a working electrode and measures a current response. See, Gunasingham et al. (1990) *J. Electroanal. Chem.* 287:349-362. The pulse signal alternates between a base potential and an excitation potential. Excitation potential pulse durations ranging from less than 100 msec to more than 1 sec are disclosed, and current sampling occurred during the last 16.7 msec of each oxidation potential pulse. See also, U.S. Pat. No. 5,312,590, which discloses applying a pulsed excitation sequence that is alternated between 0 V for 300-500 msec and 150 mV for 50-60 msec.

Furthermore, Champagne et al. disclose a voltammetric measurement method that applies variable potential signals to electrodes of an electrochemical cell to produce an electrochemical reaction and measures the resulting current response. See, U.S. Pat. No. 5,980,708. A square waveform potential was used to drive test cell electrodes. Positive and negative current responses were integrated over time periods within a current response, and the integrated currents were summed to calculate a current measurement. An example of a pulsed voltammetric measurement method disclosed therein used an input signal having a pulse height of 30 mV, a step height of 5 mV, a cycle period of 100 msec, a pulse width of 40 msec and a sample time of 35 msec. Champagne et al. further disclose ensuring that the rise time of a square wave signal applied to an electrode is sufficiently rapid to permit current measurement.

Wu et al. discloses using gated amperometric pulse sequences including multiple duty cycles of sequential excitation potentials and recoveries. See, US Patent Application Publication No. 2008/0173552. The excitation potentials provide a constant voltage to an electrochemical cell. A current response was generated during excitation potentials and measured. The current was reduced during recovery by at least half and preferably to zero. The reduced recovery current was provided by an open circuit condition to the electrochemical cell. Wu et al. thus disclose that preferred recoveries are fundamentally different from applying a zero potential recovery since these recoveries provide an independent diffusion and analyte reaction during the recovery without the effects of an applied electric potential even of zero volts.

A similar gated amperometric measurement method is disclosed by Wu, during which a recovery the electrical signal is in an off state that includes time periods when an electrical signal is not present but does not include time periods when an electrical signal is present but essentially has no amplitude. See, US Patent Application Publication No. 2009/0145779. The off state was provided by opening an electrical circuit mechanically, electrically, or by other methods. Moreover, US Patent Application Publication No. 2008/0179197 by Wu discloses gated voltammetric pulse sequences including multiple duty cycles of sequential excitations and recoveries. The excitations provided a linear, cyclic or acyclic excitation to an electrochemical cell during which response currents were measured while a applied potential was varied linearly with time. The recoveries also were provided in an open circuit condition to the electrochemical cell.

Current methods and systems therefore provide some advantages with respect to convenience; however, there remains a need for new methods of electrochemically measuring an analyte in a fluid sample even in the presence of confounding variables.

BRIEF SUMMARY

In view of the disadvantages noted above, the disclosure describes methods of electrochemically measuring an analyte in a fluidic sample such as a body fluid. The methods are based upon an inventive concept that includes using information derived from alternating current (AC) and/or DC responses, each designed to provide specific information about aspects of a biosensor and/or fluidic sample. For example, information such as current response, shape and/or magnitude from an AC block of low-amplitude signals can be used to correct for confounding variables such as Hct and/or temperature or to determine the condition of the biosensor and its suitability for providing an accurate result. Alternatively, information such as a recovery current response, shape and/or magnitude from a block of DC potentials can be used to correct for not only Hct and/or temperature but also wetting of the reagent and sample diffusion. The inventive concept therefore provides certain advantages, effects, features and objects when compared to known methods of measuring an analyte concentration (or value) in a fluidic sample.

In one aspect, an electrochemical analysis method is provided for measuring, determining, calculating or otherwise predicting an analyte concentration in a fluidic sample that has been applied to an electrochemical biosensor. The method can include at least a step of providing a test sequence of at least one DC block to the fluidic sample, where the test block is designed to elicit specific information about different aspects of the sample and/or the biosensor, where the DC block includes at least one excitation potential and at least one recovery potential, and where a closed circuit condition of an electrode system of the electrochemical biosensor is maintained during the DC block.

In another aspect, an electrochemical analysis method is provided for measuring, determining, calculating or otherwise predicting an analyte concentration in a fluidic sample that has been applied to an electrochemical biosensor. The method can include at least a step of providing a test sequence of at least one AC block and at least one DC block to the fluidic sample, where each test block is designed to elicit specific information about different aspects of the sample and/or the biosensor.

With respect to the AC block, it can be a block of low-amplitude signals applied sequentially or simultaneously in parallel. In some instances, the AC block includes at least two different low-amplitude signals. For example, the AC block can include two (2) segments at two (2) frequencies such as, for example, about 10 kHz or about 20 kHz followed by about 1 kHz or about 2 kHz. In other instances, the AC block includes a plurality of low-amplitude signals. For example, the AC block can have five (5) segments at four (4) frequencies such as, for example, about 10 kHz, about 20 kHz, about 10 kHz, about 2 kHz and about 1 kHz. Alternatively, the AC block can have four (4) segments at four (4) frequencies such as, for example, about 20 kHz, about 10 kHz, about 2 kHz and about 1 kHz. Alternatively, the AC block can have four (4) frequencies applied simultaneously at about 10 kHz, about 20 kHz, about 10 kHz, about 2 kHz and about 1 kHz. Alternately still, the AC block can have a multi-frequency excitation waveform that simultaneously applies desired low-amplitude AC signals.

In some instances, the AC block is applied for about 500 msec to about 1.5 sec. In other instances, the AC block is applied for about 100 msec to about 300 msec.

In some instances, only one AC block is applied at a beginning of a test sequence. In other instances, however, additional AC blocks can be employed and even can be interspersed with the at least one DC block. As such, the AC block can be applied before the DC block, after the DC block, or interspersed within the DC block.

While the AC segments can be applied sequentially, they also can be co-added, and the combined frequencies can be applied simultaneously in a finite block where response information can be obtained by performing a Fourier transform to obtain phase and admittance amplitude information for each AC frequency.

Regardless of the segments, frequencies and their duration, AC current response information can be obtained (i.e., measured) at any time during the AC block. In some instances, a series of AC current response measurements can be performed early in the test sequence. Measurements taken shortly after a sample is applied will be influenced by diffusion, temperature and reagent solubility. In other instances, AC measurements can be obtained at a sufficient time after an adequate sample has been applied to allow the response to stabilize, and avoid the transient response in the first second. In yet other instances, the AC response current information can be obtained up to about 160,000/sec.

In some instances, the DC block is a continuous, unipolar excitation waveform (i.e., the potential is applied and controlled throughout the DC block in a closed circuit), which is in contrast to some pulsed amperometric methods that employ an open circuit between excitation pulses. Likewise, a continuous current response can be collected, thereby allowing use of more sophisticated digital signal processing methods, such as noise filtering and signal enhancement.

In some instances, the DC block includes a plurality of short-duration excitation pulses and recovery pulses optimized for detecting an analyte such as glucose, the optimization pertaining to pulse duration, ramped transitions between the excitation pulse and recovery pulse, number of current responses measured during each pulse, and where in each pulse current response measurements are taken.

With respect to the DC block, it can include at least one (1) pulse to about ten (10) pulses at a potential that alternates between about 0 mV to about +450 mV. In some instances, the DC block can be a single potential step from about 0 mV to about +450 mV, where the potential is maintained so that a decaying current response may be detected. That is, the DC block includes at least one excitation pulse and at least one recovery pulse, where the pulses that alternate between about 0 mV to about +450 mV.

Regardless of the number of pulses, each DC pulse can be applied for about 50 msec to about 500 msec. Alternatively, each DC pulse at about +450 mV can be applied for about 250 msec, and each DC pulse at about 0 mV can be applied for about 500 msec.

In some instances, the excitation pulses and the recovery pulses are controlled during a transition up/down using ramping between the potentials. The pulses are controlled at a predetermined rate effective to mitigate a capacitive current response. Generally, the ramp rate is selected to provide about 50% or greater reduction in peak current relative to the peak current provided by a nearly ideal potential transition. For example, effective ramp rates can be from about 10 mV/msec to about 50 mV/msec.

Regardless of the number of pulses, potentials and their duration, DC current response information can be obtained at any time during the one or more DC blocks. Moreover, the DC response current information can be obtained up to about 160,000/sec.

In some instances, only one DC block is used. In other instances, a plurality of DC blocks are used. For example, a first DC block can be used to detect an analyte of interest such as glucose, and a second DC block can be used to provide information about a confounding variable. In some instances, the first DC block and the second DC block have identical ramp rates. In other instances, the second DC block has a distinct ramp rate when compared to the first DC block. Moreover, the DC block can be a waveform using at least two different ramp rates.

In some instances, the second DC block can be used to detect the analyte and thus confirm the result from the first DC block. In other instances, other DC blocks can be used to measure other electro-active analytes such as ketones in the sample.

Alternatively, the DC block can be a slow-ramp bi-polar (SRBP) waveform excitation. In some instances, the waveform can be a triangular excitation, whereas in another example it can be a sinusoidal or trapezoidal excitation.

Alternatively still, the DC block can be a waveform having multiple frequencies, and may be described by one of skill in the art of electrical engineering as a large-amplitude AC waveform, in contrast to the low-amplitude AC block as described above.

In view of the foregoing, devices, apparatuses and systems used in connection with electrochemical analysis are provided that incorporate one or more of the measurement methods disclosed herein. These devices, apparatuses and systems can be used to determine concentration of analytes including, but not limited to, amino acids, antibodies, bacteria, carbohydrates, drugs, lipids, markers, nucleic acids, peptides, proteins, toxins, viruses and other analytes, as well as combinations thereof. In certain instances, the analyte is glucose.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

Figure 1:
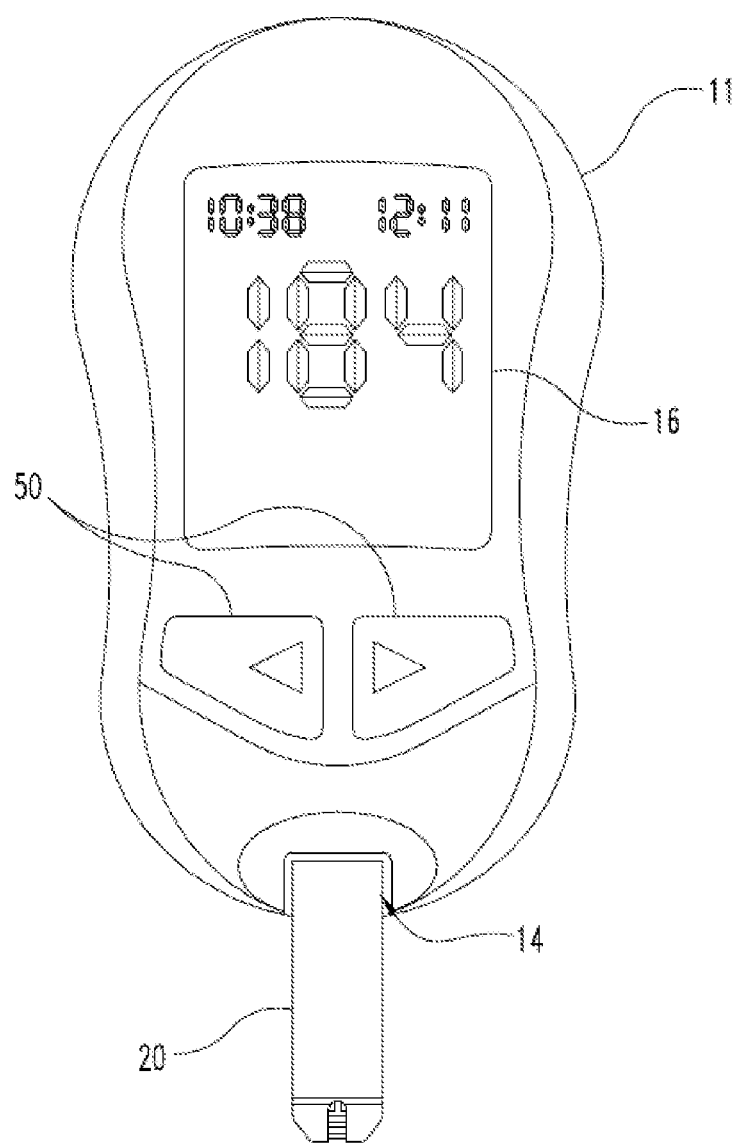
FIG. 1 shows an exemplary analyte measurement system including a meter and a biosensor.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DESCRIPTION OF EXEMPLARY EMBODIMENTS

The methods, devices, apparatuses and systems now will be described more fully hereinafter with reference to the accompanying drawings, in which some, but not all embodiments of the inventive concept are shown. Indeed, the inventive concept may be embodied in many different forms and should not be construed as limited to the embodiments set forth herein; rather, these embodiments are provided so that this disclosure will satisfy applicable legal requirements.

Likewise, many modifications and other embodiments of the methods, devices, apparatuses and systems described herein will come to mind to one of skill in the art to which the disclosure pertains having the benefit of the teachings presented in the foregoing descriptions and the associated drawings. Therefore, it is to be understood that the inventive concept is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the present methods, devices, apparatuses and systems, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

Overview

Analyte measuring methods are disclosed herein that use information derived from AC and DC current responses to provide an analyte concentration in a reliable manner. These measuring methods also can be used to reduce the effects of confounding variables such as Hct, temperature and/or variations in reagent thickness, thereby providing a more "true" analyte concentration.

The measurement methods disclosed herein largely utilize amperometry; however, it is contemplated that the methods can be used with other electrochemical measurement techniques (e.g., coulometry, potentiometry or voltammetry). Additional details regarding exemplary electrochemical measurement methods are disclosed in, for example, U.S. Pat. Nos. 4,008,448; 4,225,410; 4,233,029; 4,323,536; 4,891,319; 4,919,770; 4,963,814; 4,999,582; 4,999,632; 5,053,199; 5,108,564; 5,120,420; 5,122,244; 5,128,015; 5,243,516; 5,288,636; 5,352,351; 5,366,609; 5,385,846; 5,405,511; 5,413,690; 5,437,999; 5,438,271; 5,508,171; 5,526,111; 5,627,075; 5,628,890; 5,682,884; 5,727,548; 5,762,770; 5,858,691; 5,997,817; 6,004,441; 6,054,039; 6,254,736; 6,270,637; 6,645,368; 6,662,439; 7,073,246; 7,018,843; 7,018,848; 7,045,054; 7,115,362; 7,276,146; 7,276,147; 7,335,286; 7,338,639; 7,386,937; 7,390,667; 7,407,811; 7,429,865; 7,452,457; 7,488,601; 7,494,816; 7,545,148; 7,556,723; 7,569,126; 7,597,793; 7,638,033; 7,731,835; 7,751,864; 7,977,112; 7,981,363; 8,148,164; 8,298,828; 8,329,026; 8,377,707; and 8,420,404, as well as RE36268, RE42560, RE42924 and RE42953.

Advantageously, the methods described herein can be incorporated into SMBG devices, apparatuses and systems to more accurately and quickly report an analyte concentration, such as a glucose concentration, especially a blood glucose concentration.

Moreover, the measurement methods can be implemented using advanced microprocessor-based algorithms and processes that result in dramatically improved system performance. These measurement methods also offer flexibility and number of ways to create algorithms that can achieve improved performance such as 10/10 performance. As used herein, "10/10 performance" means that a measured bG value is within about ±10% of the actual bG value for bG concentrations >100 mg/dL, and within ±10 mg/dL of the actual bG value for bG concentrations <100 mg/dL.

Details regarding additional electrochemical measurement methods that may be useful in performing the methods disclosed herein can be found in the following co-filed and co-pending patent applications titled: "METHODS OF SCALING DATA USED TO CONSTRUCT BIOSENSOR ALGORITHMS AS WELL AS DEVICES, APPARATUSES AND SYSTEMS INCORPORATING THE SAME" (Int'l Patent Application No. PCT/EP2014/054952); "METHODS OF FAILSAFING ELECTROCHEMICAL MEASUREMENTS OF AN ANALYTE AS WELL AS DEVICES, APPARATUSES AND SYSTEMS INCORPORATING THE SAME" (Int'l Patent Application No. PCT/EP2014/054955); "METHODS OF USING INFORMATION FROM RECOVERY PULSES IN ELECTROCHEMICAL ANALYTE MEASUREMENTS AS WELL AS DEVICES, APPARATUSES AND SYSTEMS INCORPORATING THE SAME" (Int'l Patent Application No. PCT/EP2014/054943); "DESCRIPTOR-BASED METHODS OF ELECTROCHEMICALLY MEASURING AN ANALYTE AS WELL AS DEVICES, APPARATUSES AND SYSTEMS INCORPORATING THE SAME" (Int'l Patent Application No. PCT/EP2014/054956); and "METHODS OF DETECTING HIGH ANTIOXIDANT LEVELS DURING ELECTROCHEMICAL MEASUREMENTS AND FAILSAFING AN ANALYTE CONCENTRATION THEREFROM AS WELL AS DEVICES, APPARATUSES AND SYSTEMS INCORPORATING THE SAME" (Int'l Patent Application No. PCT/EP2014/054962).

Analyte Measurement Devices, Apparatuses and Systems

Prior to, and in connection with, describing the inventive measurement methods, FIG. 1 shows an exemplary analyte measurement system including a device such as a test meter 11 operatively coupled with an electrochemical biosensor 20 (also known as a test element). Meter 11 and biosensor 20 are operable to determine concentration of one or more analytes in a fluidic sample provided to the biosensor 20. In some instances, the sample may be a body fluid sample such as, for example, whole blood, plasma, serum, urine or saliva. In other instances, the fluidic sample may be another type of sample to be tested for the presence or concentration of one or more electrochemically reactive analyte(s) such as an aqueous environmental sample.

In FIG. 1, the biosensor 20 is a single use test strip removably inserted into a connection terminal 14 of meter 11. In some instances, biosensor 20 is configured as a blood glucose test element and includes features and functionalities for electrochemically measuring glucose. In other instances, biosensor 20 is configured to electrochemically measure one or more other analytes such as, for example, amino acids, antibodies, bacteria, carbohydrates, drugs, lipids, markers, nucleic acids, peptides, proteins, toxins, viruses, and other analytes.

Meter 11 includes an electronic display 16 that is used to display various types of information to the user including analyte concentration(s) or other test results, and user interface 50 for receiving user input. Meter 11 further includes a microcontroller and associated test signal generating and measuring circuitry (not shown) that are operable to generate a test signal, to apply the signal to the biosensor 20, and to measure one or more responses of the biosensor 20 to the test signal. In some instances, meter 11 can be configured as a blood glucose measurement meter and includes features and functionalities of the ACCU-CHEK® AVIVA® meter as described in the booklet "Accu-Chek® Aviva Blood Glucose Meter Owner's Booklet" (2007), portions of which are disclosed in U.S. Pat. No. 6,645,368. In other instances, meter 11 can be configured to electrochemically measure one or more other analytes such as, for example, amino acids, antibodies, bacteria, carbohydrates, drugs, lipids, markers, nucleic acids, proteins, peptides, toxins, viruses, and other analytes. Additional details regarding exemplary meters configured for use with electrochemical measurement methods are disclosed in, for example, U.S. Pat. Nos. 4,720,372; 4,963,814; 4,999,582; 4,999,632; 5,243,516;

5,282,950; 5,366,609; 5,371,687; 5,379,214; 5,405,511; 5,438,271; 5,594,906; 6,134,504; 6,144,922; 6,413,213; 6,425,863; 6,635,167; 6,645,368; 6,787,109; 6,927,749; 6,945,955; 7,208,119; 7,291,107; 7,347,973; 7,569,126; 7,601,299; 7,638,095 and 8,431,408.

One of skill in the art understands that the measurement methods described herein can be used in other measurement, devices, apparatuses, systems and environments such as, for example, hospital test systems, laboratory test systems and others.

It shall be understood that the biosensor and meter can include additional and/or alternate attributes and features in addition to or instead of those shown in FIG. 1. For example, the biosensor can be in the form of a single use, disposable electrochemical test strip having a substantially rectangular shape. It shall be appreciated that the biosensors can include different forms such as, for example, test strips of different configurations, dimensions or shapes, non-strip test elements, disposable test elements, reusable test elements, micro-arrays, lab-on-chip devices, bio-chips, bio-discs, bio-cds or other test elements. Additional details regarding exemplary biosensors configured for use with electrochemical measurement methods are disclosed in, for example, U.S. Pat. Nos. 5,694,932; 5,762,770; 5,948,695; 5,975,153; 5,997,817; 6,001,239; 6,025,203; 6,162,639; 6,245,215; 6,271,045; 6,319,719; 6,406,672; 6,413,395; 6,428,664; 6,447,657; 6,451,264; 6,455,324; 6,488,828; 6,506,575; 6,540,890; 6,562,210; 6,582,573; 6,592,815; 6,627,057; 6,638,772; 6,755,949; 6,767,440; 6,780,296; 6,780,651; 6,814,843; 6,814,844; 6,858,433; 6,866,758; 7,008,799; 7,063,774; 7,238,534; 7,473,398; 7,476,827; 7,479,211; 7,510,643; 7,727,467; 7,780,827; 7,820,451; 7,867,369; 7,892,849; 8,180,423; 8,298,401; 8,329,026, as well as RE42560, RE42924 and RE42953.

Figure 2:
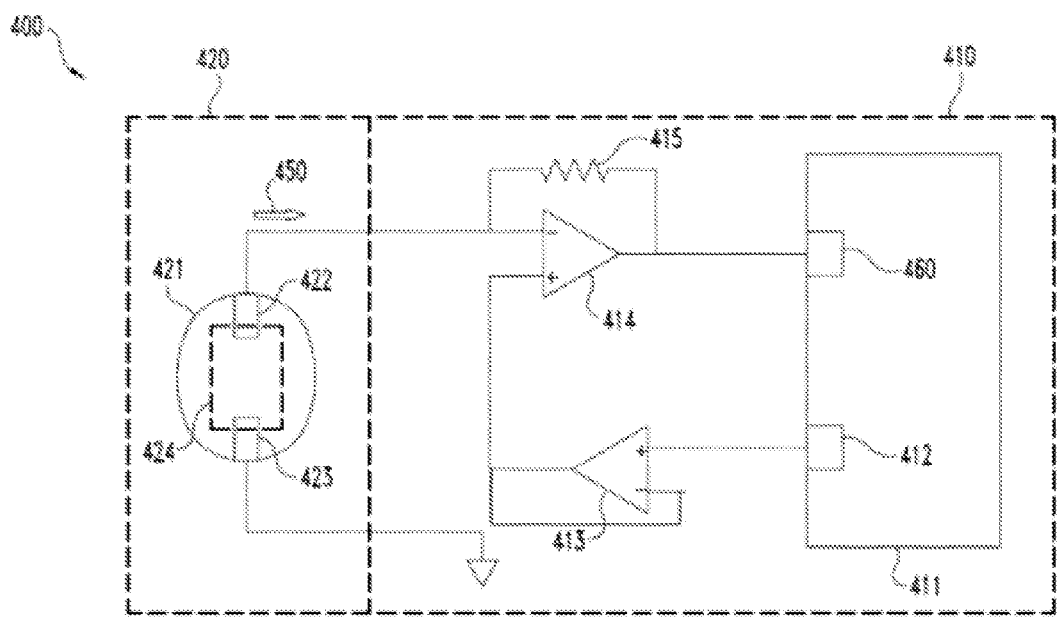
FIG. 2 shows a simplified circuit diagram for an exemplary analyte measurement system.

FIG. 2 shows a simplified circuit diagram 400 of an exemplary analyte measurement system including a biosensor 420 operatively coupled with a meter 410 to provide electrical communication between biosensor 420 and meter 410. Biosensor 420 includes a test cell 421 having a working electrode 422 and a counter electrode 423 in contact with a combined reagent and sample 424. Working electrode 422 is in electrical communication with the negative input of amplifier 414 of meter 410. Counter electrode 423 is in electrical communication with a virtual ground or reference potential of meter 410.

Meter 410 includes a microcontroller 411, which is operable to generate and output a test control signal at output 412. The test control signal drives amplifier 413 to output a test potential to the positive input of amplifier 414. This test potential is also seen at the negative input of amplifier 414 due to a virtual short between the positive input and negative input of amplifier 414. The test potential present at the negative input of amplifier 414 provided to working electrode 422. Thus, the test control signal output by microcontroller 411 is operable to control the test potential applied to the working electrode 422. The test control signal provided at output 412 and test potential provided to working electrode 422 may include a number features such as AC components, preconditioning components, and DC pulse sequences including excitation potentials and closed circuit recovery potentials, examples of which are further described herein below.

The test potential applied to working electrode 422 produces a current response 450 that is provided to the negative input of amplifier 414. Amplifier 414 is configured as an I/V converter and outputs a voltage to input 460 of microcontroller 411 that is proportional to current response 450. Microcontroller 411 detects the voltage at input 460 and determines the current response 450 by dividing the voltage seen at input 460 by the value of gain resistor 415. The current response 450 may include responses to test potentials including AC components, preconditioning components, and DC pulse sequences including excitation potentials and closed circuit recovery potentials, examples of which are further described herein below.

It shall be appreciated that additional exemplary analyte measurement systems may include a number of features in addition to or as alternatives to those illustrated in simplified circuit diagram 400. For example, microcontroller 411 also may be operatively connected to other components of meter 410 such as one or more digital memories, displays, and/or user interfaces, such as those illustrated and described above in connection with FIG. 1, as well as controller and driver circuitry associated therewith. In FIG. 2, output 412 is an analog output connected to a D/A converter internal to microcontroller 412, and input 460 is an analog input connected to an A/D converter internal to microcontroller 412. In other instances, output 412 may be a digital output connected to an external D/A converter and input 460 may be a digital input connected to an external A/D converter. In FIG. 2, test cell 421 is a two-electrode test cell; however, other test cells can be three-electrode test cells, or other electrode systems.

In FIG. 2, a test potential can be applied to a working electrode to provide a potential difference between the working electrode and a counter electrode. Alternatively, a test potential other than virtual ground or reference potential can be provided as a counter electrode to provide a potential difference between the working electrode and a counter electrode. It shall be appreciated that the foregoing and a variety of other additional and alternate test cell, electrode, and/or circuitry configurations operable to apply a test signal to an electrode system in contact with a combined sample and reagent and measure a response thereto may be utilized.

Measurement Methods

As noted above, the measurement methods described herein are based upon an inventive concept that includes using information derived from AC and/or DC current responses to a test sequence having at least one AC block and/or at least one DC block, each block designed to provide specific information about aspects of a fluidic sample and/or biosensor.

Figure 3:
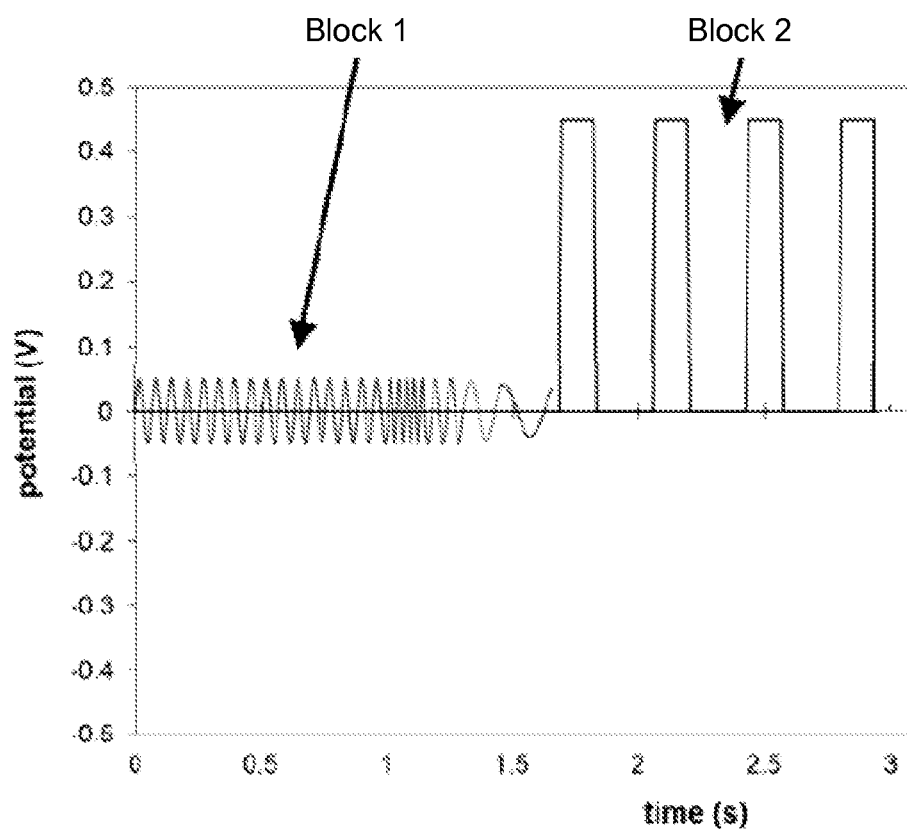
FIG. 3 shows an exemplary test sequence that may be employed by an analyte measuring device, apparatus or system.

The methods generally include applying to a fluidic sample, such as a body fluid, an AC block of low-amplitude signals in connection with a DC block having a controlled, pulsed sequence and measuring the AC and DC current responses. FIG. 3 shows an exemplary test sequence and response thereto that may be used in connection with SMBGs and other test systems. The test sequence thus includes an AC block of low-amplitude signals followed by a controlled, DC block of excitation pulses and recovery pulses.

With respect to the AC block, it can include a plurality of AC segments such as, for example, from about 2 segments to about 10 segments, from about 3 segments to about 9 segments, from about 4 segments to about 8 segments, from about 5 segments to about 7 segments, or about 6 segments. In other instances, the AC block can include about 2 segments, about 3 segments, about 4 segments, about 5 segments, about 6 segments, about 7 segments, about 8 segments, about 9 segments, or about 10 segments. In still other instances, the AC block can have more than 10 segments, that is, about 15 segments, about 20 segments, or about 25 segments. In yet other instances, the AC block can include 1 segment, where the segment has multiple low-amplitude AC signals applied simultaneously.

One of skill in the art understands that the number of segments in the AC block will be limited by the complexity of the response, the associated frequency range and time available to perform the measurements. Higher frequencies generally require high bandwidth electronics and faster sampling, whereas lower frequencies take longer and are typically noisier. The maximum number of segments therefore will be a compromise of these parameters, choosing the minimum count and frequency span needed to discriminate the sample and environmental and/or confounding factors of interest.

As used herein, "about" means within a statistically meaningful range of a value or values such as a stated concentration, length, molecular weight, pH, potential, time frame, temperature, voltage or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

The frequency of each signal in each segment of the AC block can be from about 1 kHz to about 20 kHz, from about 2 kHz to about 19 kHz, from about 3 kHz to about 18 kHz, from about 4 kHz to about 17 kHz, from about 5 kHz to about 16 kHz, from about 6 kHz to about 15 kHz, from about 7 kHz to about 14 kHz, from about 8 kHz to about 13 kHz, from about 9 kHz to about 12 kHz or from about 10 kHz to about 11 kHz. In other instances, the frequency of each segment in the AC block can be about 1 kHz, about 2 kHz, about 3 kHz, about 4 kHz, about 5 kHz, about 6 kHz, about 7 kHz, about 8 kHz, about 9 kHz, about 10 kHz, about 11 kHz, about 12 kHz, about 13 kHz, about 14 kHz, about 15 kHz, about 16 kHz, about 17 kHz, about 18 kHz, about 19 kHz, or about 20 kHz. In still other instances, the frequency of each signal in each segment of the AC block can be more than 20 kHz, that is, about 30 kHz, about 40 kHz, or about 50 kHz. In some instances, one or more of the segments can have the same frequency, whereas in other instances each segment has a distinct frequency from the other segments. Four frequencies, however, generally is adequate. The exact frequencies employed can be readily generated by simple integer division of a measurement system clock's maximum frequency.

A maximum frequency limit for a signal in a segment of the AC block, however, can be up to about 100 kHz for an inexpensive, battery-powered handheld instrument. Beyond that, the increasing demands on analog bandwidth, sampling rate, storage and processing speed quickly add up, while the imaginary portion of a typical biosensor response becomes increasingly smaller with frequency. Lower frequencies have longer periods and take longer times to sample with comparable accuracy.

The AC block typically includes at least two different low-amplitude signals. For example, the AC block can include two (2) segments at two (2) frequencies such as, for example, about 10 kHz or about 20 kHz followed by about 1 kHz or about 2 kHz. In other instances, the AC block includes a plurality of low-amplitude signals. For example, the AC block can have five (5) segments at four (4) frequencies such as, for example, about 10 kHz, about 20 kHz, about 10 kHz, about 2 kHz and about 1 kHz. Alternatively, the AC block can have four (4) segments at four (4) frequencies such as, for example, about 20 kHz, about 10 kHz, about 2 kHz and about 1 kHz. Alternatively, the AC block can have four (4) frequencies applied simultaneously at about 10 kHz, about 20 kHz, about 10 kHz, about 2 kHz and about 1 kHz. Alternately still, the AC block can have a multi-frequency excitation waveform that simultaneously applies the desired low-amplitude AC signals. The AC frequencies may be applied sequentially, or combined and applied simultaneously and analyzed via Fourier Transform.

The AC block can be applied for about 500 msec to about 1.5 sec, about 600 msec to about 1.25 sec, about 700 msec to about 1000 msec, or about 800 msec to about 900 msec. Alternatively, the AC block can be applied for about 500 msec, about 600 msec, about 700 msec, about 800 msec, about 900 msec, about 1000 msec, about 1.25 sec or about 1.5 sec. In particular, the AC block can be applied for about 100 msec to about 300 msec.

One of skill in the art, however, understands that the number, frequency, duration and order of the AC segments can be varied.

AC current response information can be obtained at any time during a test sequence. Impedance results at lower frequencies may be influenced by analyte concentration if obtained after an electrochemical cell is DC polarized. In some instances, a series of AC current response measurements can be obtained early in the test sequence. Measurements taken shortly after a fluidic sample is applied to a biosensor will be influenced by diffusion, temperature and reagent solubility. In other instances, the AC response current measurements can be obtained at a sufficient time after an adequate sample has been applied to allow the response to stabilize, and avoid the transient response in the first second. Likewise, response current measurements can be made at one or more frequencies. Due to their capacitive nature, multiple AC measurements separated by a frequency octave or decade may offer different sensitivities or easier manipulation.

Accurate measurements can be more difficult at frequencies above 5 kHz but can offer increased visibility to the real impedance. Here, frequencies at 20 kHz, 10 kHz, 2 kHz and 1 kHz were used. In addition, the frequencies were applied in this sequence to simplify measurement electronics and to allow the lower frequencies (larger imaginary impedances) longer to stabilize.

Additional details regarding exemplary AC blocks in electrochemical measurement methods are disclosed in, for example, U.S. Pat. Nos. 7,338,639; 7,390,667; 7,407,811; 7,417,811; 7,452,457; 7,488,601; 7,494,816; 7,597,793; 7,638,033; 7,751,864; 7,977,112; 7,981,363; 8,148,164; 8,298,828; 8,377,707 and 8,420,404.

With respect to the DC block, it typically includes a constantly applied potential difference that alternates between about 0 mV and a predetermined positive potential difference, or other slowly time-varying potential difference that can be analyzed by traditional DC electrochemical methods. One of skill in the art, however, understands that the range for the applied potential difference can, and will, vary depending upon the analyte and reagent chemistry used.

The DC block can include a plurality of pulses such as, for example, from about 2 pulses to about 10 pulses, from about 3 pulses to about 9 pulses, from about 4 pulses to about 8 pulses, from about 5 pulses to about 7 pulses, or about 6 pulses. In other instances, the DC block can include about 2 pulses, about 3 pulses, about 4 pulses, about 5 pulses, about 6 pulses, about 7 pulses, about 8 pulses, about 9 pulses, or about 10 pulses. In still other instances, the DC block can have more than 10 pulses, that is, about 15 pulses, about 20 pulses, or about 25 pulses. As used herein, "pulse" means at least one excitation and/or one recovery period. The number of pulses, however, typically is limited by the available time for the test sequence. Shorter durations probe further from the electrode surface, and increase sensitivity to reagent thickness and diffusion modifiers.

The potential of each pulse in the DC block can be from about 0 mV to about 450 mV, from about 10 mV to about 425 mV, from about 15 mV to about 400 mV, from about 20 mV to about 375 mV, from about 25 mV to about 350 mV, from about 30 mV to about 325 mV, from about 35 mV to about 300 mV, from about 40 mV to about 275 mV, from about 45 mV to about 250 mV, from about 50 mV to about 225 mV, from about 75 mV to about 200 mV, from about 100 mV to about 175 mV, or from about 125 mV to about 150 mV. In other instances, the potential of each pulse in the DC block can be about 1 mV, about 10 mV, about 15 mV, about 20 mV, about 25 mV, about 30 mV, about 35 mV, about 40 mV, about 45 mV, about 50 mV, about 60 mV, about 70 mV, about 80 mV, about 90 mV, about 100 mV, about 110 mV, about 120 mV, about 130 mV, about 140 mV, about 150 mV, about 160 mV, about 170 mV, about 180 mV, about 190 mV, about 200 mV, about 210 mV, about 220 mV, about 230 mV, about 240 mV, about 250 mV, about 260 mV, about 270 mV, about 280 mV, about 290 mV, about 300 mV, about 310 mV, about 320 mV, about 330 mV, about 340 mV, about 350 mV, about 360 mV, about 370 mV, about 380 mV, about 390 mV, about 400 mV, about 410 mV, about 420 mV, about 430 mV, about 440 mV, or about 450 mV. In still other instances, the potential of each pulse of the DC block can be more than 450 mV, that is, about 475 mV, about 500 mV, about 525 mV, about 550 mV, about 575 mV, about 600 mV kHz, about 625 mV, about 650 mV, about 675 mV, about 700 mV, about 725 mV, or about 750 mV. In still other instances, the excitation pulse potential can be greater-than, less-than or equal to about +450 mV. In some instances, one or more of the pulses can have the same potential, whereas in other instances each pulse has a distinct potential from the other pulses.

As noted above, the applied DC potential can be fixed at about 0 mV between excitation pulses to provide a recovery pulse, thus making it a generally continuous, unipolar excitation waveform. This is in contrast to a test signal sequence from known techniques that prescribe the use of an open circuit between positive DC pulses, thereby excluding the possibility of collecting and analyzing the current between positive pulses.

Regardless of the number, each DC pulse can be applied for about 50 msec to about 500 msec, about 60 msec to about 450 msec, about 70 msec to about 400 msec, about 80 msec to about 350 msec, about 90 msec to about 300 msec, about 100 msec to about 250 msec, about 150 msec to about 200 msec, or about 175 msec. Alternatively, each pulse can be applied for about 50 msec, about 60 msec, about 70 msec, about 80 msec, about 90 msec, about 100 msec, about 125 msec, about 150 msec, about 175 msec, about 200 msec, about 225 msec, about 250 msec, about 275 msec, about 300 msec, about 325 msec, about 350 msec, about 375 msec, about 400 msec, about 425 msec, about 450 msec, about 475 msec or about 500 msec. In particular, each DC pulse at +450 mV can be applied for about 250 msec, and each DC pulse at 0 mV can be applied for about 500 msec. Alternatively still, each pulse can be applied for less than about 50 msec or more than about 500 msec. The duration should be long enough or the onset soft enough to avoid charging currents. Regardless, the pulse duration should be applied long enough to enable reasonable 50/60 Hz noise rejection. Moreover, the time between pulses is ideally long enough to allow the electrochemical cell to discharge and return close to its pre-pulse state. Furthermore, the operating potential will depend upon the mediator and measurement system. The examples herein demonstrate proof-of-principal with NA-derived redox mediator.

Generally, the ramp rate of each pulse is selected to provide about 50% or greater reduction in peak current relative to the peak current provided by a nearly ideal potential transition. In some instances, each pulse can have the same ramp rate. In other instances, some pulses can have the same ramp rate and other pulses can have a different ramp rate. In still other instances, each pulse has its own ramp rate. For example, effective ramp rates can be from about 5 mV/msec to about 75 mV/msec or from about 10 mV/msec to about 50 mV/msec, 15 mV/msec to about 25 mV/msec, or about 20 mV/msec. Alternatively, the ramp rate can be about 5 mV/msec, about 10 mV/msec, about 15 mV/msec, about 20 mV/msec, about 25 mV/msec, about 30 mV/msec, about 35 mV/msec, about 40 mV/msec, about 45 mV/msec, about 50 mV/msec, about 55 mV/msec, about 60 mV/msec, about 65 mV/msec, about 70 mV/msec, or about 75 mV/msec. In particular, the ramp rate can be from about 40 mV/msec to about 50 mV/msec.

To determine the excitation potential for a given redox mediator, one may plot current measured a fixed time after a selected working electrode/counter-electrode (WE-CE) potential step is applied (e.g., 3.5 sec). In any case, one of skill in the art would strive to operate comfortably on a current-potential plateau. Higher potentials, however, are not always better as they can invite other (i.e., interfering) reactions that may undesirably contribute to the analyte measurement of interest.

In some instances, the test sequence includes a single DC block, whereas in other instances the test sequence includes two or more DC blocks.

An exemplary DC block can alternate (i.e., pulse) between about 0 mV and about +450 mV (in biamperometric mode).

Like the AC block, one of skill in the art understands that the number, potential, duration and order of the DC pulses can be varied.

In the methods, the AC and/or DC response current information can be obtained (i.e., measured or recorded) at about 2,000/sec to about 200,000/sec, at about 3,000/sec to about 190,000/sec, at about 4,000/sec to about 180,000/sec, at about 5,000/sec to about 170,000, at about 6,000/sec to about 160,000/sec, at about 7,000/sec to about 150,000/sec, at about 8,000/sec to about 140,000/sec, at about 9,000/sec to about 130,000/sec, at about 10,000/sec to about 120,000/sec, at about 15,000/sec to about 110,000/sec, at about 20,000/sec to about 100,000/sec, at about 30,000/sec to about 90,000/sec, at about 40,000/sec to about 80,000/sec, at about 50,000/sec to about 70,000/sec, or at about 60,000/sec. In some instances, the AC and/or DC response current information can be obtained at about 100/sec to about 200/sec, at about 200/sec to about 300/sec, at about 300/sec to about 400/sec, at about 400/sec to about 500/sec, at about 500/sec to about 600/sec, at about 600/sec to about 700/sec, at about 700/sec to about 800/sec, at about 800/sec to about 900/sec, at about 1,000/sec to about 1,500/sec, at about 1,500/sec to about 2,000/sec, at about 2,000/sec to about 2,500/sec, at about 2,500/sec to about 3,000/sec, at about 3,000/sec to about 3,500/sec, at about 3,500/sec to about 4,000/sec, at about 4,000/sec to about 4,500/sec, at about 4,500/sec to about 5,000/sec, at about 5,000/sec to about 5,500/sec, at about 5,500/sec to about 6,000/sec, at about 6,000/sec to about 6,500/sec, at about 6,500 to about 7,000/sec, at about 7,000/sec to about 7,500/sec, at about 7,500/sec to about 8,000/sec, at about 8,000/sec to about 8,500/sec, at about 8,500 to about 9,000/sec, at about 9,000/sec to about 9,500/sec, at about 9,500/sec to about 10,000/sec, at about 10,000/sec to about 20,000/sec, at about 20,000/sec to about 30,000/sec, at about 30,000/sec to about 40,000/sec, at about 40,000/sec to about 50,000/sec, at about 50,000/sec to about 60,000/sec, at about 60,000/sec to about 70,000/sec, at about 70,000/sec to about 80,000/sec, at about 80,000/sec to about 90,000/sec, at about 90,000/sec to about 100,000/sec, at about 100,000/sec to about 110,000/sec, at about 110,000/sec to about 120,000/sec, at about 120,000/sec to about 130,000/sec, at about 130,000/sec to about 140,000/sec, at about 140,000/sec to about 150,000/sec, at about 150,000/sec to about 160,000/sec, at about 160,000/sec to about 170,000/sec, at about 170,000/sec to about 180,000/sec, at about 180,000/sec to about 190,000/sec, or at about 200,000/sec. In other instances, the AC and/or DC response current information can be obtained up to about 100/sec, about 200/sec, about 300/sec, about 400/sec, about 500/sec, 600/sec, about 700/sec, about 800/sec, about 900/sec, about 1,000/sec, about 1,250/sec, about 1,500/sec, about 1,750/sec, about 2,000/sec, about 2,225/sec, about 2,500/sec, about 2,750/sec, about 3,000/sec, about 3,250/sec, about 3,500/sec, about 3,750/sec, about 4,000/sec, about 4,250/sec, about 4,500/sec, about 4,750/sec, about 5,000/sec, about 5,250/sec, about 5,500/sec, about 5,750/sec, about 6,000/sec, about 6,250/sec, about 6,500, about 7,000/sec, about 7,250/sec, about 7,500/sec, about 7,750/sec, about 8,000/sec, about 8,250/sec, about 8,500/sec, about 8,750, about 9,000/sec, about 9,250/sec, about 9,500/sec, about 9,750/sec, about 10,000/sec, about 15,000/sec, about 20,000/sec, about 25,000/sec, about 30,000/sec, about 35,000/sec, about 40,000/sec, about 45,000/sec, about 50,000/sec, about 55,000/sec, about 60,000/sec, about 65,000/sec, about 70,000/sec, about 75,000/sec, about 80,000/sec, about 85,000/sec, about 90,000/sec, about 95,000/sec, about 100,000/sec, about 105,000/sec, about 110,000/sec, about 115,000/sec, about 120,000/sec, about 125,000/sec, about 130,000/sec, about 135,000/sec, about 140,000/sec, about 145,000/sec, about 150,000/sec, about 155,000/sec, about 160,000/sec, about 165,000/sec, about 170,000/sec, about 175,000/sec, about 180,000/sec, about 185,000/sec, about 190,000/sec, about 195,000 or at about 200,000/sec. In yet other instances, the AC and/or DC response current information can be obtained at more than 200,000/sec.

Taken together, the at least one AC block and the at least one DC block encompass the test sequence that is applied to the sample. As illustrated in FIG. 3, an exemplary test sequence therefore can include: (1) an AC block of a plurality of AC segments at different frequencies; and (2) a DC block of short-duration (e.g., about 50-500 msec) about 450-mV pulses separated by similarly short-duration (e.g., about 50-500 msec) recovery pulses, during which a closed circuit about 0-mV recovery potential is applied.

Stated differently, an exemplary test sequence therefore can include three (3) blocks that may be executed in any order. A first AC block can begin after a fluidic sample is detected and confirmed on a biosensor. The initial first sec is a 10 kHz, small amplitude AC waveform to monitor the dynamics of reagent dissolution and reaction dynamics. This is followed by four (4) 150 msec AC segments of 20 kHz, 10 kHz, 2 kHz and 1 kHz. A second block can be a series of DC pulses, where a positive applied potential difference is of sufficient amplitude and duration to induce a diffusion-limited current. These pulses are interlaced with a lesser potential difference that are not of a sufficient amplitude to induce a diffusion-limited current and long enough to allow the cell to return near its pre-pulse state. A third block also can be a series of DC pulses, such as an SRBP.

Current response information is collected from the test sequence and includes current responses to the AC and DC blocks. In some instances, the current response information can be collected at an A/D sampling rate for DC and AC measurements to simplify the system design, including a single shared signal path for AC and DC measurements. Common digital audio sampling rates range include, but are not limited to, from about 44.1 kHz to about 192 kHz. A/D converters in this range are readily available from variety of commercial semiconductor suppliers.

Current response information to the AC block can be used to determine impedance, admittance and phase values or other complex parameters as described in further detail below. Likewise, current information to the DC block can be used to determine analyte concentration or other complex parameters as described in further detail below.

Figure 4:
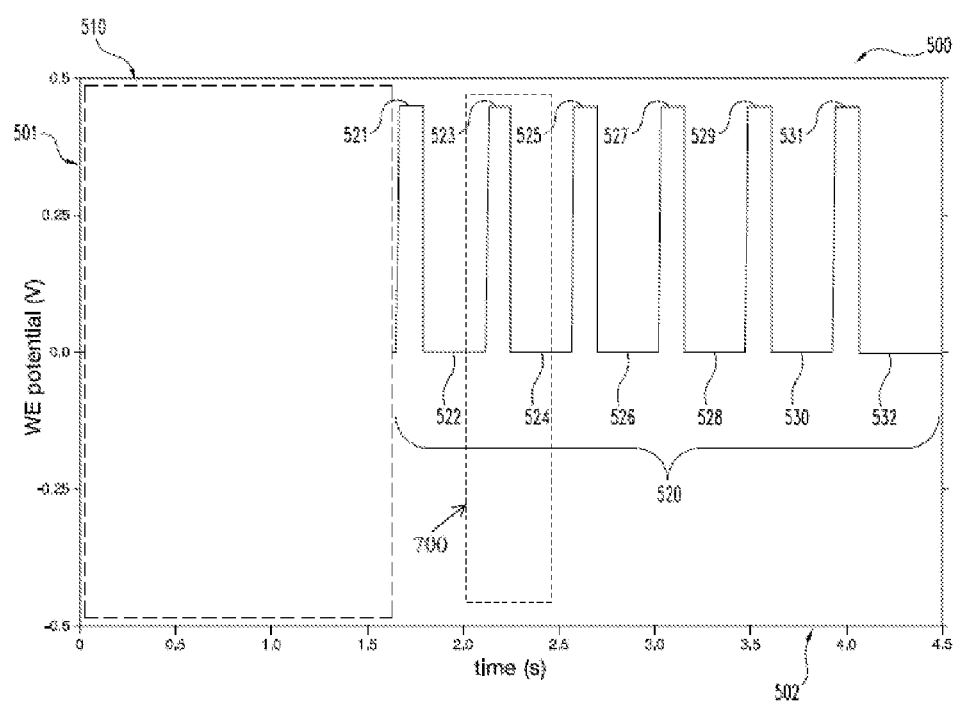
FIG. 4 is a graph of an exemplary test sequence of an analyte measurement system.
Figure 5:
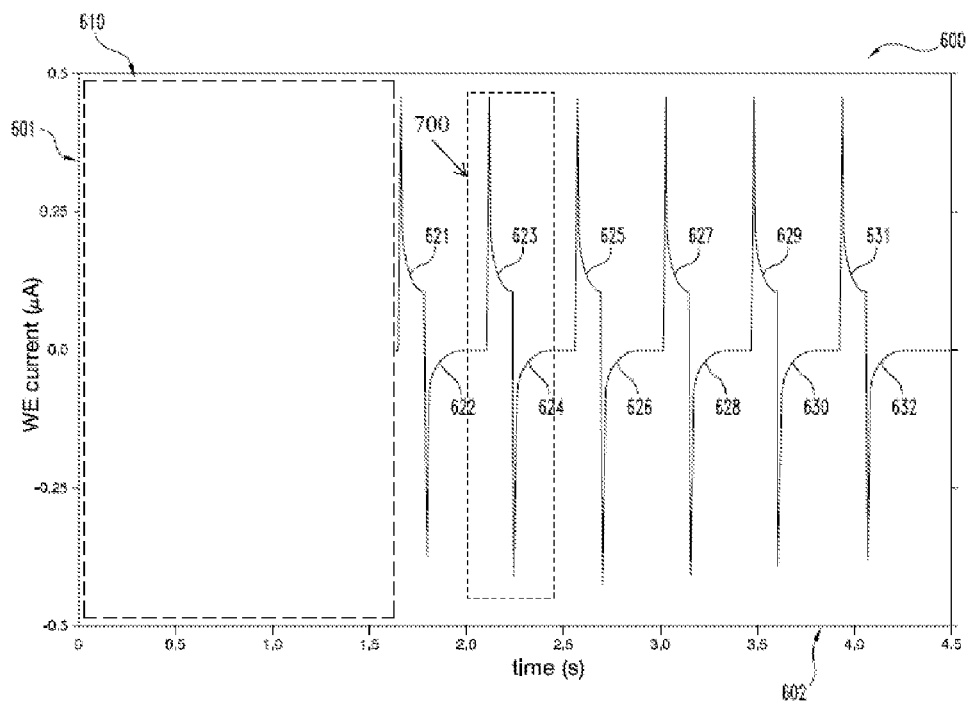
FIG. 5 is a graph of an exemplary response of an analyte measurement system.

As shown in FIGS. 4-5, one trace illustrates the applied DC potential, and the other trace illustrates the AC and DC current responses, respectively. As noted above, the applied DC potential can be fixed at about 0 mV between pulses to provide a recovery pulse, thus making it a generally continuous excitation waveform. This is in contrast to a test sequence from known techniques that prescribe the use of an open circuit between positive DC pulses, thereby excluding the possibility of collecting and analyzing the current between positive excitation pulses. As used herein, "recovery pulse" means an about zero-potential pulse applied for an adequately long recovery period in which the electrochemical reaction with the analyte of interest (e.g., glucose) is turned "off," thereby allowing the system to return to a fixed starting point before subsequent interrogation with another more positive DC pulse.

As part of the inventive concept, it has been recognized that the recovery responses in the DC block include unique informational content, particularly pertaining to Hct and temperature. Furthermore, this information provides value and can be utilized to further refine accuracy and performance of SMBG devices, apparatuses and systems.

Returning to FIG. 4, the responses to the pulsed DC block encode Hct and temperature information, as well as real-time information about other important processes, such as wetting of the reagent, sample diffusion and separation with respect to the reagent, the establishment of a stable glucose transport gradient, and the kinetics associated with the reducible analyte. The illustrated DC block provides short, distinct strobing of these processes with respect to time. Each positive DC pulse produces a distinct current signature, which is not exactly like the others due to its position in time.

Importantly, each closed circuit recovery potential pulse provides an adequately long recovery period in which the electrochemical reaction with glucose is turned off, thereby allowing the system to return to a common starting point before subsequent interrogation with another positive pulse.

Just as the shapes of the current decays from positive DC pulses encode information about glucose, Hct and temperature (as well as the other biosensor processes noted above), the shapes of the recovery pulses also are unique. Each recovery pulse produces a negative current response with a rate of growth that also encodes distinct, time-ordered information describing how the biamperometric system returns to a given reference state. The rate of current growth during the recovery pulse is not simply a mirror image of the current decay associated with a neighboring positive DC pulse, because the glucose reaction has been turned off by selecting a potential magnitude that cannot initiate and sustain the electrochemical reaction with glucose. The exemplary measurement methods disclosed herein use unique information content pertaining to Hct, temperature and other confounding variables encoded by the recovery current responses to improve the accuracy and performance SMBG devices, apparatuses and systems.

It shall be appreciated that near-zero, and non-zero positive and negative potential magnitudes also may be used as recovery pulses in additional embodiments, and that the magnitude, duration, and shapes of all pulses may vary from the illustrated exemplary embodiments. It shall also be appreciated that the exemplary embodiments disclosed herein do not restrict the number of AC signals that may be employed, their positions in time, or their amplitude(s)/frequencies. Nor does it restrict interspersing AC signals within the pulsed DC block of the test sequence, such as in the exemplary test signal illustrated in FIG. 4 and discussed in greater detail below. Furthermore, the exemplary embodiments disclosed herein do not restrict the number, length or magnitude of the DC pulses.

FIG. 4 shows an exemplary test sequence 500 that can be provided to an electrode system of an electrochemical test cell. The vertical axis 501 of graph denotes working electrode potential in volts (V). It shall be understood that working electrode potential may refer to a potential applied to a working electrode or to a potential difference between a working electrode and another electrode such as a counter or reference electrode regardless of the electrode or electrodes to which a potential or a test signal is applied. The horizontal axis 502 of graph denotes time in sec. Test sequence 500 is applied at or after time=0 sec, which is a time at which a sufficient sample is present in a test cell as may be determined using sample sufficiency detection electrodes and signals or through other methods.

Test sequence 500 begins with a signal component 510 (or block) that may include one or more AC segment(s), preconditioning test segment(s) or combinations thereof. Signal component 510 also may include incubation signal components that are selected not to drive an electrochemical reaction but to allow for reagent hydration and progression of reaction kinetics. Such incubation components may include, for example, an open circuit condition, a 0 mV potential, a substantially 0 mV average potential, or a non-zero volt potential such as a non-zero potential that is less than the potential needed to drive a particular reaction of interest.

In some instances, signal component 510 comprises one or more AC sequences and frequencies provided to an electrode system of an electrochemical test cell. For example, the AC segments of signal component 510 include a 10 kHz segment applied from about time=0 sec to about time=1.2 sec, a 20 kHz segment applied from about time=1.2 sec to about time=1.3 sec, a 10 kHz segment applied from about time=1.3 sec to about time=1.4 sec, a 2 kHz segment applied from about time=1.4 sec to about time=1.5 sec, and a 1 kHz segment applied from about time=1.5 sec to about time=1.6 sec. Alternatively, the AC segments and frequencies of signal component 510 includes a 10 kHz signal applied for about 1.5 sec, followed by a 20 kHz signal applied for about 0.2 sec, followed by a 10 kHz signal applied for about 0.2 sec, followed by a 2 kHz signal applied for about 0.2 sec, followed by a 1 kHz signal applied for about 0.2 sec.

As noted above, the signal component 510 can include one or more preconditioning signal(s). In some instances, the signal component 510 includes a positive DC preconditioning pulse applied starting at about time=0 sec for about 200-600 msec and having an amplitude of about 100 mV or greater. In other instances, the signal component 510 can include a positive DC preconditioning pulse applied starting at about time=0 sec for about 500 msec and having an amplitude of about 450 mV. In still other instances, the signal component 510 can include a two-cycle triangular potential waveform including a ramp rate of about 2 mV/msec.

As such, the signal component 510 can include combinations of one or more AC segments as well as preconditioning signal component(s). In some instances, the signal component 510 includes one or more AC signal components followed by one or more preconditioning signal components. In other instances, the signal component 510 includes one or more preconditioning signal components followed by one or more AC signal components.

After signal component 510, a pulsed DC sequence 520 (or block) is applied to the electrode system. Pulse sequence 520 begins with the working electrode potential being ramped up to the excitation potential of pulse 521. From pulse 521 the working electrode potential is ramped down to the recovery potential of pulse 522. From potential 522 the working electrode potential is sequentially ramped up and down to the potentials of pulses 523-532. As shown in FIG. 4, the ramp rate between pulses is controlled to occur at a predetermined rate effective to mitigate capacitive current response. In some instances, the ramp rate is selected to provide a 50% or greater reduction in peak current relative to the peak current provided by a substantially square wave excitation in which signal rise time is determined by the native characteristics of the driving circuitry rather than being deliberately controlled according to a predetermined target rate or range.

Pulses 521, 523, 525, 527, 529 and 531 are examples of ramp-rate controlled excitation potential pulses that provide an excitation potential to an electrochemical test cell effective to drive an electrochemical reaction in the test cell and generate an associated Faradaic current response which may be convolved with capacitive charging current responses and other current response information attributable to a plurality of confounding variables. As also shown in FIG. 4, the excitation potential pulses provide a potential difference between a working electrode and a counter electrode of about 450 mV that is about 130 msec in duration. The excitation potential shown is selected to drive a particular analyte reaction, which in this case is an enzyme-mediated reaction of glucose. It shall be understood that the magnitude and duration of the excitation potential pulses may vary depending upon the particular activation potential of the mediator used or the potential needed to drive a particular reaction of interest.

Pulses 522, 524, 526, 528, 530 and 532 are examples of closed circuit recovery potential pulses that provide a potential to a working electrode of an electrochemical test cell during which a closed circuit condition of the test cell is maintained to control the test cell to discharge current and to more rapidly restore test cell conditions to a substantially common starting point for subsequent interrogation with an excitation potential pulse. Closed circuit recovery potential pulses also may be ramp rate controlled in the same or a similar manner to excitation potential pulses. As shown in FIG. 4, the recovery potential pulses provide a potential difference between a working electrode and a counter electrode of about 0 mV, which is about 280 msec in duration during which the electrode system is maintained in a closed circuit condition.

In some instances, the magnitude of the DC potential provided by a closed circuit recovery pulse and its duration may vary depending upon the potential below which a test cell can recover toward a pre-excitation state and the time needed to provide a desired response. Thus, some embodiments can include recovery potential pulses having a non-zero potential that is less than the activation potential of a given mediator. Some instances include recovery potential pulses having a non-zero potential that is less than the potential needed to drive a particular reaction of interest. Other instances include recovery potential pulses having a non-zero potential that is less than the minimum redox potential for a specified reagent system. Still other instances include recovery potential pulses having an average potential of about 0 mV, but which have pulse portions greater than about 0 mV and portions less than about 0 mV. Still other instances include recovery potential pulses having an average potential according to any of the aforementioned non-zero potentials, but which have portions greater than the non-zero average and portions less than the non-zero average.

FIG. 5 shows a response signal 600 produced by a test cell in response to test signal 500 of FIG. 4. The vertical axis 601 of graph 600 denotes working electrode current in μA. The horizontal axis 602 of graph 600 denotes time in seconds. Current response 600 begins with response component 610 that includes a response to signal component 510. In some instances, response component 610 includes AC current responses from which impedance, admittance and phase angle can be determined. Such measurements may be performed for one or more AC block segments or components such as those described above in connection with FIG. 4. In some instances, signal component 610 includes a preconditioning signal component but no AC segment and no measurement of response component 610 is performed. In other instances, signal component 610 includes a combination of the foregoing and/or other components.

After response component 610, response signal 600 includes a sequence of exponentially decaying excitation current responses 621, 623, 625, 627, 629 and 631, which are generated in response to excitation pulses 521, 523, 525, 527, 529 and 531, respectively. Excitation current responses 621, 623, 625, 627, 629 and 631 include a Faradaic current response component relating to an electrochemical reaction in the test cell as well as a capacitive charging current response relating to capacitive electrode charging and current response information attributable to a plurality of confounding variables. Current responses 622, 624, 626, 628, 630 and 632 include a recovery current response relating to discharge of the test cell when maintained in a closed circuit condition applying a recovery potential and current response information attributable to a plurality of confounding variables.

Current responses 621-632 include information related to the concentration of an analyte of interest that may be present in the fluidic sample being tested, as well as additional information of confounding variables convolved therewith. This inventive concept described herein therefore can be incorporated into methods by which the information associated with current responses 621-631 can be used to determine a concentration of an analyte of interest with enhanced accuracy, precision, repeatability and reliability by compensating for or decreasing sensitivity to one or more confounding variables. A number of confounding variables may impact analyte concentration determinations including variations in reagent film thickness, sample temperature, sample Hct, reagent wetting, and reaction kinetics among others. The present disclosure demonstrates that the methods disclosed herein may be utilized to perform analyte concentration determinations that compensate for or exhibit decreased sensitivity to such confounding variables.

Figure 6:
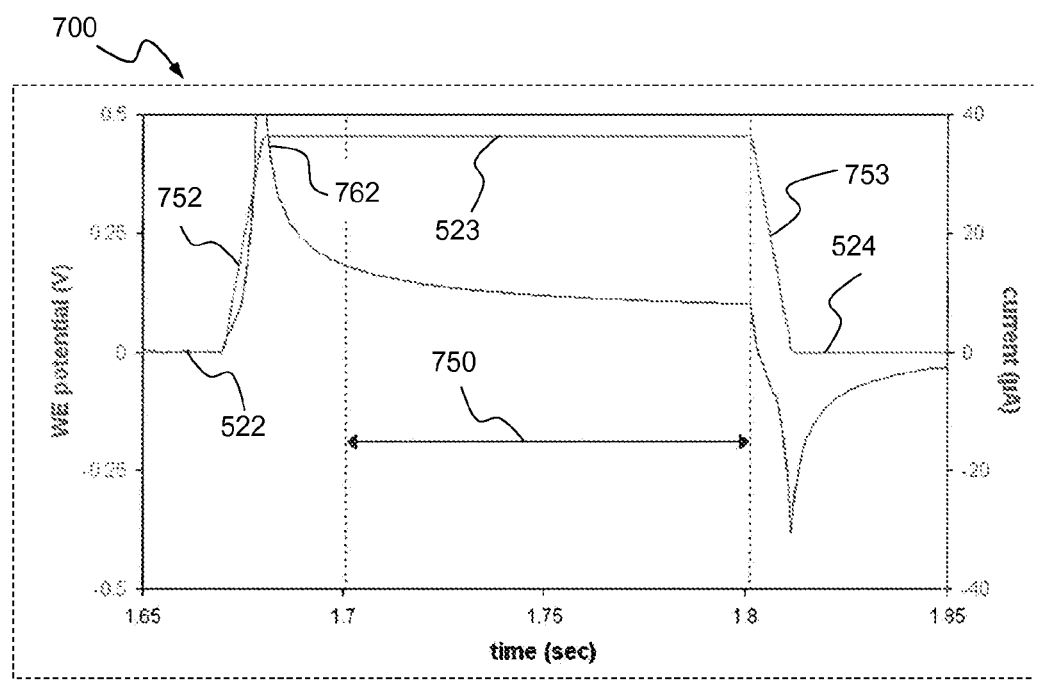
FIG. 6 is an enlarged view illustrating portions of the test sequence of FIG. 4 and the response of FIG. 5.

FIG. 6 shows in greater detail a portion 700 of the signals illustrated in FIGS. 4-5. The closed circuit recovery potential 522 ramps to excitation potential 523 over a rate controlled ramp potential 752 such as, for example, a ramp rate of about 45 mV/msec. Other embodiments control the ramp rate between pulses at different rates that are effective to reduce the contribution of the effect of capacitive charging on current responses.

The ramping rate of ramp potential 752 is effective to reduce the effect of capacitive charging on current response 762, which is generated in response to ramp potential 752 and excitation potential 523. Current is measured starting about 30 msec after excitation potential 523 is achieved over an about 100 msec measurement period ending at the point at which excitation potential 523 begins to ramp down to closed circuit recovery potential 522 over ramp potential 753. Similar current measurements may be taken for excitation current responses 621, 625, 627, 629 and 631. It shall be appreciated that average current measurements may be performed using continuous integration, discrete integration, sampling or other averaging techniques. The successive current measurements may be used to construct an effective current decay curve from which analyte concentration can be calculated using techniques such as Cottrell analysis and others. In FIG. 6, ramp potential 752, ramp potential 753 is controlled to have a ramp rate substantially the same as ramp potential 752. In other instances, ramp potential 753 may be controlled at different rates or may be allowed to transition at a system defined rate without active control.

In connection with ramp rates, it can be seen in FIG. 6 that one may observe a high peak response when a potential is applied (see, the initial current response 762 on that shoots above the graph as the potential is ramped up to about +450 mV, as well as the current response as the potential is ramped down to about 0 mV). To protect components of the measurement meter or system and/or to prevent interference with the electrochemical reaction, it may be necessary to shunt the initially observed current response and/or the lastly observed current response. A shunting switch could be closed when sensor currents may exceed the maximum allowable input current to prevent an I-V amplifier from saturating. Alternatively, or in addition, it may be necessary to exclude the ramped parts of the current response and use response information from a measurement window 750 as shown in FIG. 6.

Current responses, such as current responses 621-632, therefore encode unique time ordered information relating to sample glucose concentration, sample Hct, sample temperature, as well as information relating to processes such as reagent wetting of the reagent, sample diffusion and separation with respect to the reagent, the establishment of a stable glucose transport mechanism, and the kinetics associated with the reducible analyte. Pulse sequences such as pulse sequence 520 provide short, distinct strobing of these processes with respect to time and produces current responses including unique, time-ordered information relating to sample glucose concentration, sample Hct, sample temperature, and other factors. The inventors have demonstrated a number of unexpected advantages of the methods disclosed herein through experiments in which pulse sequences such as pulse sequence 520 were used to analyze various concentrations of blood glucose while Hct and temperature were varied systematically.

Figure 7A:
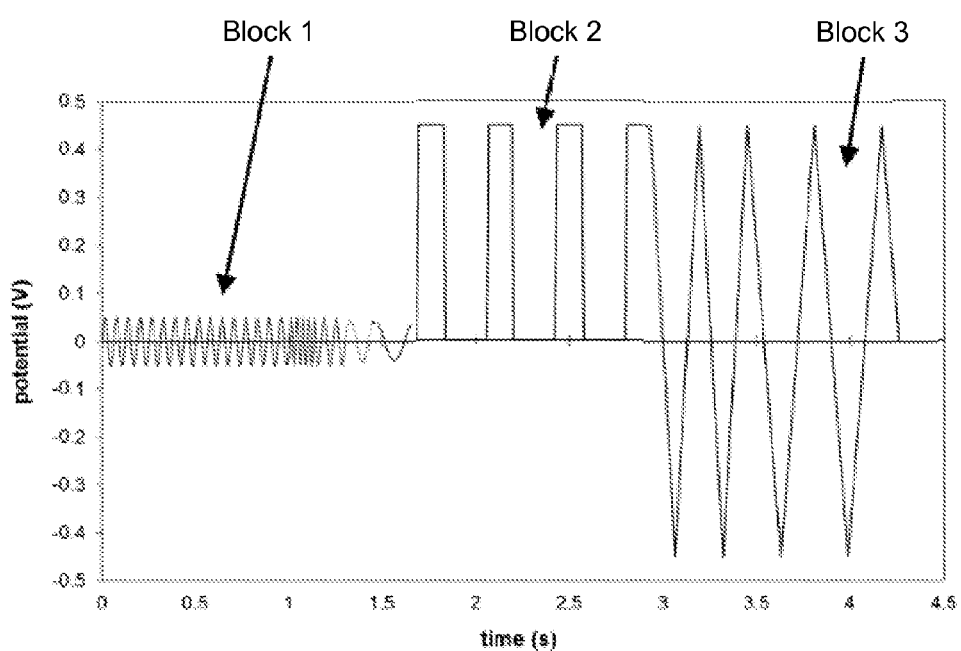
FIG. 7A shows another exemplary test sequence that may be employed by an analyte measurement system.
Figure 7B:
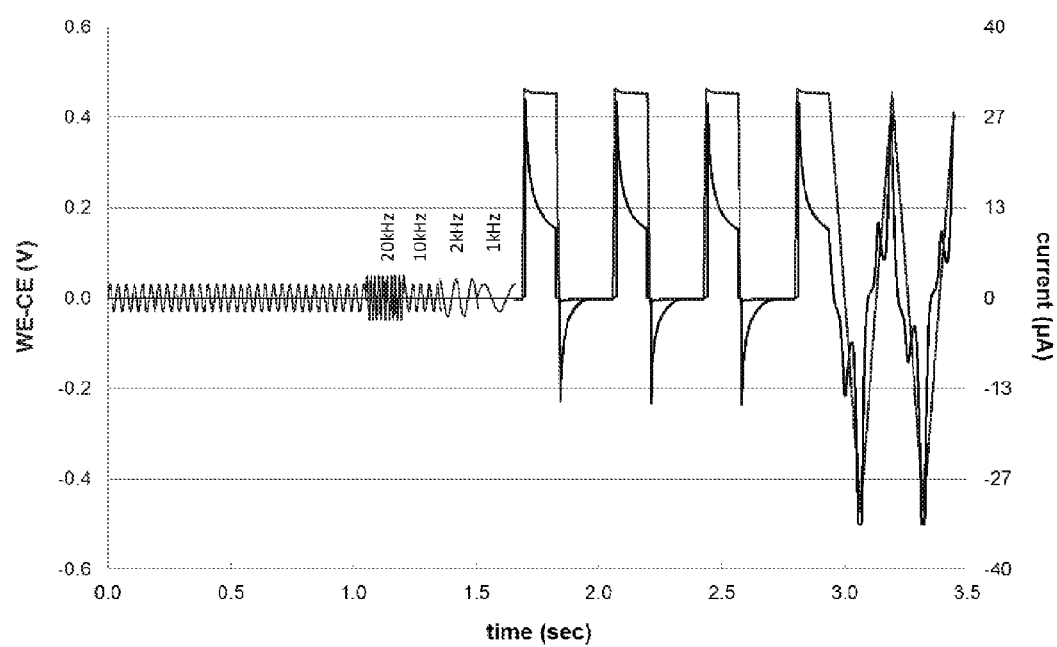
FIG. 7B shows a more detailed exemplary test sequence that may be employed by the analyte measurement system.

FIG. 7A shows another exemplary test sequence of (1) an AC block (labeled AC Block) including a plurality of low-amplitude signals; (2) a DC block (labeled DC Block 1) including short +450 mV pulses separated by relaxation potentials at 0 mV, where the mediator is not oxidized by the applied potential; and (3) a second DC block (labeled DC Block 2) including a slow-ramped, bi-polar potential (SRBP) at two different ramp rates. More specifically, and as shown in FIG. 7B, the AC block includes five (5) segments different at four (4) frequencies, namely 10 kHz, 20 kHz, 10 kHz, 2 kHz and 1 kHz. Current response information to the AC block may be used to determine admittance and phase values or other complex parameters as described in further detail below. In some instances, an analyte concentration determination, such as a bG determination, is performed based upon current response information from the AC block and current response information from DC Block 1. Current response information from DC Block 2, however, may be used for constructing a glucose failsafe.

The second DC block shown in FIGS. 7A-B arose out of research relating to SRBP excitation sequences. In theory, any DC excitation with sufficient potential to cause an electrochemical reaction of mediator on the electrodes will produce a current response that can be used to quantitatively measure an analyte such as glucose. This current response also will be impacted by changing Hct and temperature levels. This research assessed the value of SRBP test sequences to determine whether additional, unique information could be obtained and used to improve analyte measurement system performance and/or capabilities, in much the same way that the use of recovery pulse information in combination with excitation pulse information can be used to improve performance.

At the frequencies used, the current response to the first AC block in FIG. 7B does not contain information about glucose because the amplitude of the signal is below the redox potential for the reagent-analyte system, but it does encode information about Hct, temperature, and other factors, which can be used to correct a blood glucose (bG) reading derived from the DC test block(s). The current response to DC Block 1 corresponds primarily to an amount of, for example, phenylenediamine (PDA; part of a known bG mediator system), which is proportional to the amount of glucose present. In contrast, the current response to DC Block 2 provides quantitative information about levels of, for example, quinonediimine (QDI; also part of the bG mediator system), as well as PDA. Like DC Block 1, the current responses at +450 mV and −450 mV correspond to PDA, and are proportional to the amount of glucose present. However, the SRBP also enables the detection of QDI at lower, mid-range applied potentials during the negative- and positive-going applied potential ramps.

Figure 8:
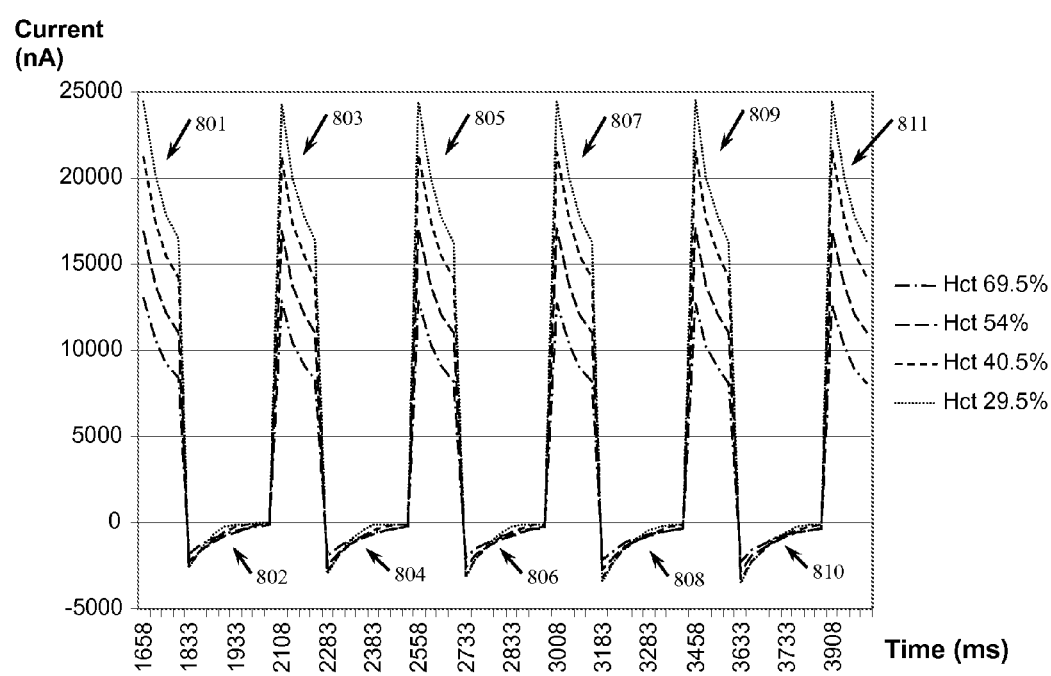
FIG. 8 is a graph illustrating current responses for test samples with varying Hct concentrations, constant temperatures, and constant glucose concentrations.

FIG. 8 shows the effects of an exemplary systematic variation of excitation current responses and recovery current responses to pulse sequence 520 described above for varying Hct and constant temperature. Current response sequences are illustrated for four test samples with varying Hct concentrations of about 29.5%, 40.5%, 54% and 69.5%, constant glucose concentrations of about 530 mg/dL, and constant temperatures of about 25° C. The magnitude and decay rates of the excitation current responses to excitation potential pulses 521, 523, 525, 527, 529 and 531 vary with sample Hct in a manner that is substantially constant with respect to time. At each Hct, current responses 801, 803, 805, 807, 809 and 811 exhibit substantially consistent magnitudes and decay rates for each pulse in pulse sequence 520. Within each pulse of pulse sequence 520, the magnitude of current responses 801, 803, 805, 807, 809 and 811 varies in an inverse relationship with Hct.

The magnitude and growth rates of the recovery current responses to recovery potential pulses 522, 524, 526, 528, 530 and 532 also exhibit an observable relationship. Recovery current responses 802, 804, 806, 808 and 810 to closed circuit recovery potential pulses 522, 524, 526, 528, 530 and 532 have comparable starting magnitudes both within each pulse and across pulses for each Hct, but have different rates of growth resulting in current response crossovers. As Hct varies, current responses 802, 804, 806, 808 and 810 grow at different rates depending upon the Hct. The aforementioned current response characteristics and relationships also were demonstrated in experiments that used samples having constant glucose concentrations of about 33 mg/dL but were otherwise substantially in accordance with those described above.

Figure 9:
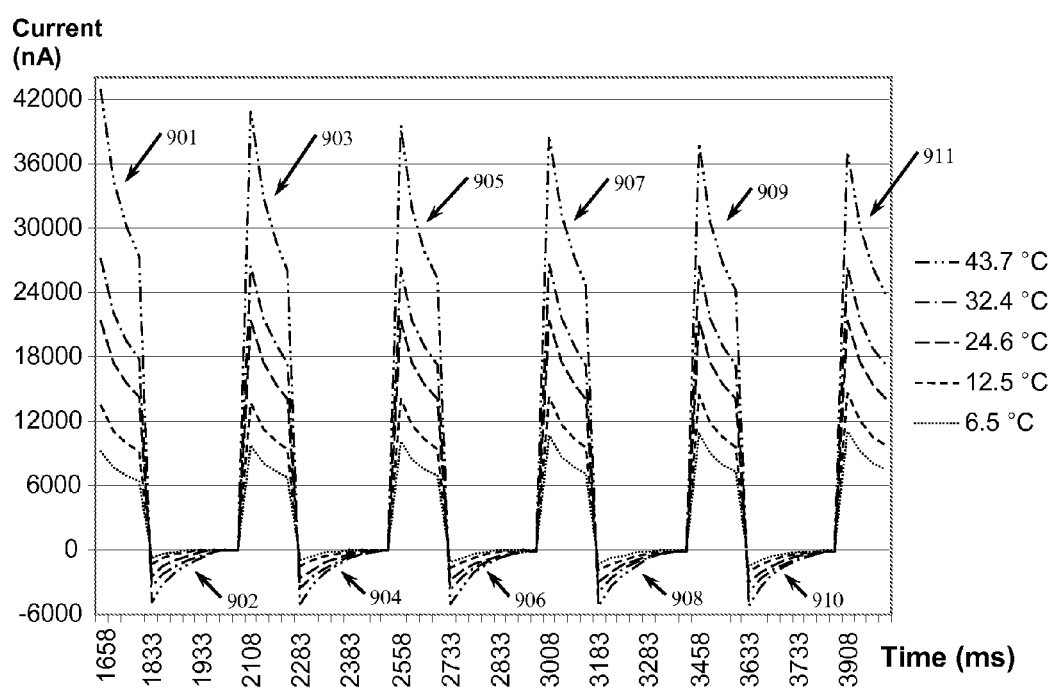
FIG. 9 is a graph illustrating current responses for test samples with varying temperatures, constant Hct concentrations and constant glucose concentrations.

In comparison, FIG. 9 shows the effects an exemplary systematic variation of current responses to pulse sequence 520 for varying temperature, constant Hct and constant glucose concentration. Current responses are illustrated for five test samples with varying temperatures of 6.5° C., 12.5° C., 24.6° C., 32.4° C. and 43.7° C., constant Hct of about 41%, and constant glucose concentrations of about 535 mg/dL. The current responses to the positive DC potential of pulses 521, 523, 525, 527, 529 and 531 show a relative decrease for successive pulses with respect to time. The magnitude of current responses 901, 903, 905, 907, 909 and 911 decrease successively across pulses for each of the sample temperatures. Furthermore, the amount of decrease across pulses varies depending upon sample temperature.

The magnitude and growth rates of the recovery current responses 902, 904, 906, 908 and 910 to recovery potential pulses 522, 524, 526, 528, 530 and 532 also exhibit an observable relationship. Recovery current responses 902, 904, 906, 908 and 910 show substantially consistent magnitudes across pulses and, within each pulse, have distinctly ordered starting values and decreasing growth rates, but exhibit no crossover. The aforementioned current response characteristics and relationships also were demonstrated in experiments that used samples having constant glucose concentrations of about 33 mg/dL but were otherwise substantially in accordance with those described above.

From this research, a number of current determination methods will now be described that use information from excitation current responses and closed circuit recovery responses disclosed herein that compensate for or increase insensitivity to variation in sample temperature, sample Hct, or both. According to certain methods, a current value is determined from the current responses to pulsed sequences such as those described herein and is used to calculate analyte concentration according to the Cottrell equation.

In one example, current was determined based upon a combination of the last measurement point in one excitation current response and one closed circuit recovery response. This current determination compensated for and exhibited decreased sensitivity to variation in sample temperature and variation in sample Hct relative to current determinations based upon only excitation current response information.

Likewise, the measurement methods can be used to compensate for or increase insensitivity to variation in reagent thickness or to increased analyte measurement insensitivity to variation in reagent thickness. Exemplary methods are demonstrated in a series of experiments, the results of which are shown in FIGS. 10-14. The experiments measured working electrode current responses to a test signal including a sequence of DC excitation pulses and closed circuit recovery pulses similar to those disclosed herein above for varying reagent film thicknesses.

Figure 10:
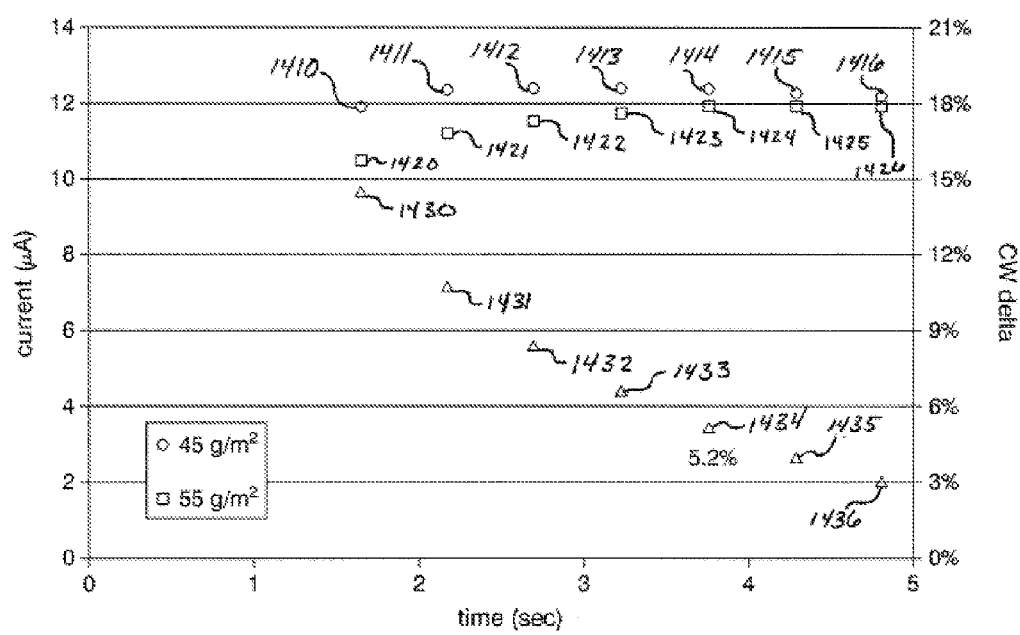
FIG. 10 is a graph illustrating current responses and current response deltas for a first exemplary test sequence.

FIG. 10 shows current responses to a DC pulse sequence in which a working electrode potential was ramped between excitation potential pulses about +450 mV in amplitude and about 130 msec in duration and closed circuit recovery potential pulses about 0 mV in amplitude and about 280 msec in duration. Current response measurements were taken during the last 100 msec of each excitation potential pulse. Current responses 1410-1416 represent an average current measured during the last 100 msec of the excitation potential pulses applied to a test element with a reagent film thickness of about 4.4 µM was provided by application of a wet coat weight of about 45 g/m². Current responses 1420-1426 represent an average current measured during the last 100 msec of the excitation potential pulses applied to a biosensor with a reagent film thickness of about 5.5 m was provided by application of a wet coat weight of about 5.5 g/m².

FIG. 10 further shows current deltas (Δ) 1430-1436, which denote the percent delta between current response measurements 1410-1416 and corresponding current measurements 1420-1426. As shown by current response 1434, a current response delta of about 5.2% was achieved at about 3.7 sec after sample detection. In contrast, the corresponding current response deltas for a constant DC potential of about 450 mV applied before and maintained after sample dosing remained above about 8% as late as 5 sec after sample detection. Similarly, the current response deltas for a stepped DC potential of about 450 mV applied about 3 sec after sample dosing and maintained thereafter remained above about 8% as late as 5 sec after sample detection.

Figure 11:
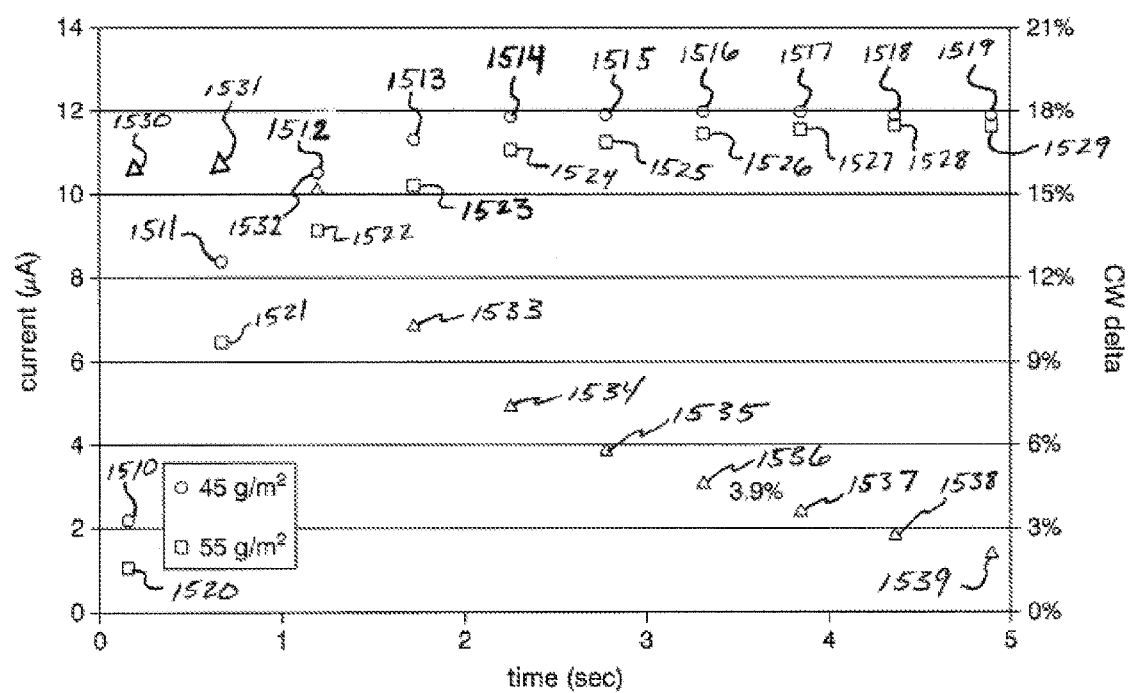
FIG. 11 is a graph illustrating current responses and current response deltas for a second exemplary test sequence.

FIG. 11 shows current responses to a DC pulse sequence similar to that of FIG. 10, but for ten (10) excitation potential pulses applied starting immediately after a sample is detected. Current responses 1510-1519 represent an average current measured during the last 100 msec of the excitation potential pulses applied to a test element with a reagent film thickness of about 4.4 µm. Current responses 1520-1529 represent an average current measured during the last 100 msec of the excitation potential pulses applied to a test element with a reagent film thickness of about 5.5 µm. Current deltas 1530-1539 illustrate that the current deltas due to reagent film thickness are initially comparable to those of FIG. 10, but decrease to about 3.9% at about 3.7 sec after sample detection.

Figure 12:
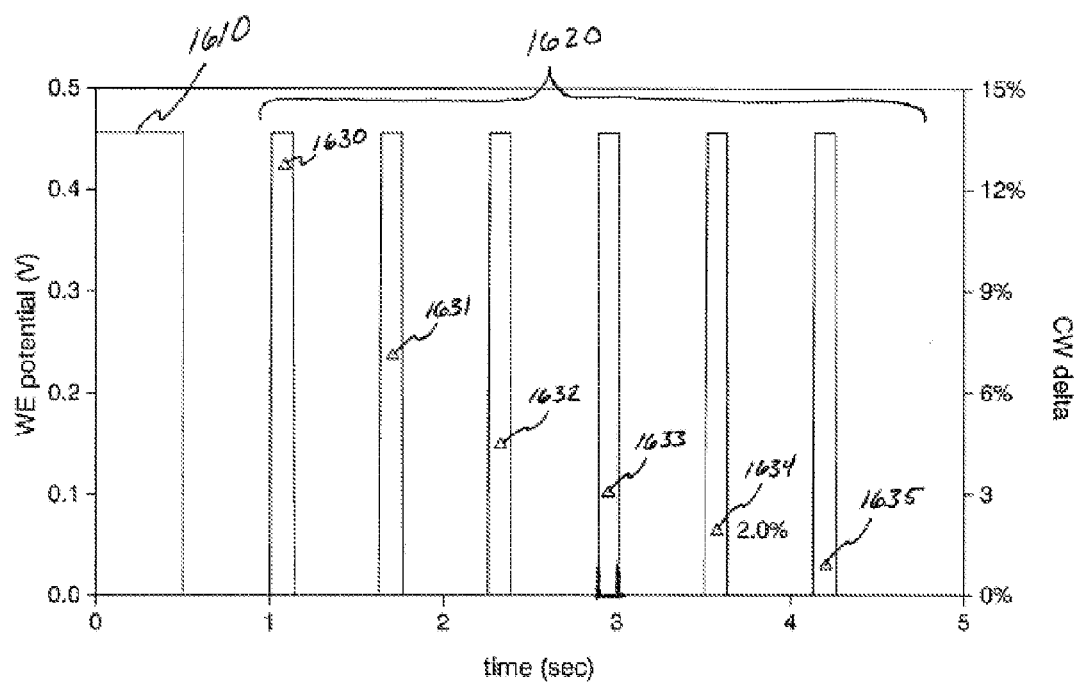
FIG. 12 is a graph illustrating another exemplary test signal and current response deltas for the third exemplary test signal.

FIG. 12 shows a test sequence in which a preconditioning potential 1610 of about 450 mV and about 500 msec in duration was applied to a working electrode at sample detection. About 1 sec after sample detection, a DC pulse sequence 1620 was applied in which working electrode potential was ramped between excitation potential pulses about 450 mV in amplitude and about 130 msec in duration and closed circuit recovery potential pulses about 0 mV in amplitude and about 280 msec in duration. FIG. 12 further shows current deltas 1630-1635, which indicate the difference between the average current measured during the last 100 msec of the excitation potential pulses for reagent film thicknesses of about 4.4 µM and 5.5 µm. Here, a current response delta of about 2% was achieved at about 3.7 sec after sample detection.

Further experimentation involving preconditioning pulses similar to that used in connection with FIG. 12 revealed that pulses with the same polarity as subsequent excitation pulses were effective to decrease current measurement deltas for variations in reagent thickness. This experimentation also revealed that the reduction in such current deltas increased as the magnitude of the preconditioning pulses increased.

Figure 13:
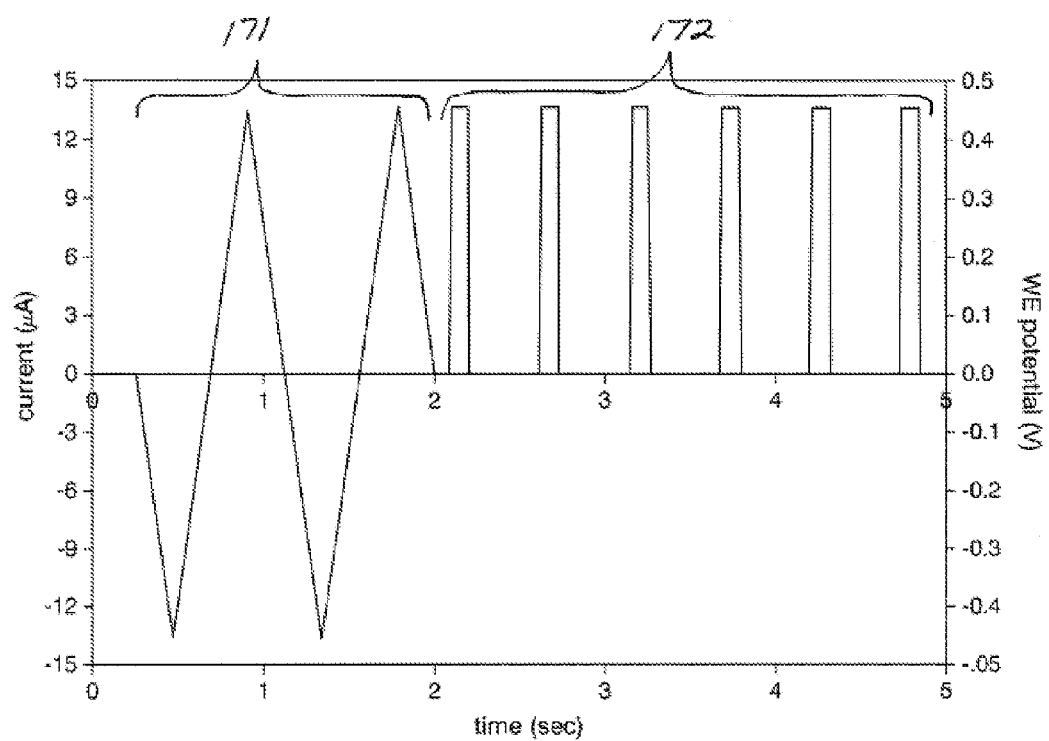
FIG. 13 is a graph illustrating another exemplary test signal.

FIG. 13 shows a test sequence in which a two-cycle triangular preconditioning waveform 171 that alternates between a potential of −450 mV and +450 mV and is about 1800 msec in duration and that was applied to a working electrode about sample detection. Starting about 200 msec after sample detection, a DC pulse sequence 172 was applied, in which working electrode potential was ramped between excitation potential pulses about +450 mV in amplitude and about 130 msec in duration and closed circuit recovery potential pulses about 0 mV in amplitude and about 280 msec in duration.

Figure 14:
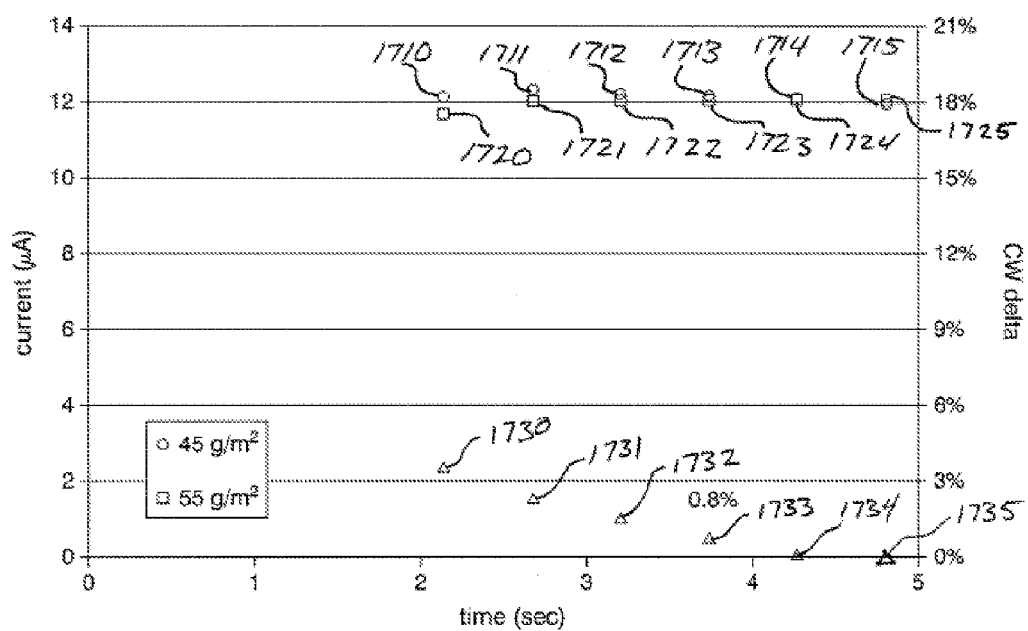
FIG. 14 is a graph illustrating current responses and current response deltas to the fourth exemplary test signal of FIG. 13.

FIG. 14 illustrates a graph of current responses and current response deltas corresponding to the test sequence of FIG. 13. Current responses 1710-1715 represent an average current measured during the last 100 msec of the excitation potential pulses applied to a test element with a reagent film thickness of about 4.4 µm. Current responses 1720-1725 represent an average current measured during the last 100 msec of the excitation potential pulses applied to a test element with a reagent film thickness of about 5.5 µm. Current deltas 1730-1735 illustrate that the current deltas due to dry film thickness are initially lower than those of FIGS. 10-11 and decrease to about 0.8% about 3.7 sec after sample detection.

All of the patents, patent applications, patent application publications and other publications recited herein are hereby incorporated by reference as if set forth in their entirety.

The present invention has been described in connection with what are presently considered to be the most practical and preferred embodiments. However, the invention has been presented by way of illustration and is not intended to be limited to the disclosed embodiments. Accordingly, one of skill in the art will realize that the invention is intended to encompass all modifications and alternative arrangements within the spirit and scope of the invention as set forth in the appended claims.

The invention claimed is:

1. A method of electrochemically measuring an analyte in a fluid sample, the method comprising the steps of:
   applying an electrical test sequence to an electrochemical biosensor, the biosensor comprising:
   an electrode system,
   a reagent in electrical communication with the electrode system, and
   a receptacle configured to contact the fluid sample provided to the biosensor,
   with the fluid sample in fluidic contact with the reagent, wherein the test sequence comprises at least two blocks, each block configured to produce response information to the test sequence, wherein one block is an alternating current (AC) block and another block is a direct current (DC) block, wherein the DC block includes at least one recovery potential, and wherein a closed circuit condition of the electrode system is maintained during the DC block;
   measuring the information from the response to the test sequence, including information from the at least one recovery potential; and
   determining an analyte concentration of the fluid sample using the information, the determining based at least in part upon the information from the at least one recovery potential.

2. The method of claim 1, wherein the AC block is applied before the DC block, after the DC block or interspersed within the DC block.

3. The method of claim 1, wherein the AC block is applied before the DC block.

4. The method of claim 1, wherein the AC block comprises a multi-frequency excitation waveform of at least two different frequencies.

5. The method of claim 4, wherein the frequencies of the AC block are about 10 kHz, about 20 kHz, about 10 kHz, about 2 kHz and about 1 kHz, and wherein each frequency is applied for about 0.5 seconds to about 1.5 seconds.

6. The method of claim 1, wherein the DC block comprises a pulsed sequence alternating between an excitation potential and the at least one recovery potential, and wherein the determining comprises determining an effective current based upon the information of the excitation current response and the recovery current response and determining the analyte concentration based upon the effective current.

7. The method of claim 6, wherein the pulsed sequence includes at least one pulse to about ten pulses, wherein the excitation pulse is at about +450 mV and the recovery pulse is at about 0 mV, and wherein each pulse is applied for about 50 msec to about 500 msec.

8. The method of claim 7, wherein each excitation pulse at about +450 mV is applied for about 250 msec and each recovery pulse at about 0 mV is applied for about 500 msec.

9. The method of claim 6, wherein a ramp rate between the excitation pulse and recovery pulse is controlled to be within a predetermined range, and wherein the ramp rate is from about 10 mV/msec to about 50 mV/msec.

10. The method of claim 1, wherein the information of the response to the test sequence is selected from the group consisting of current response, duration, shape and magnitude.

11. The method of claim 1, further comprising the step of correcting an effect on the analyte concentration by at least one confounding variable from the information obtained from the recovery potential.

12. The method of claim 11, wherein the at least one confounding variable is selected from the group consisting of hematocrit, temperature and variation in thickness of the reagent.

13. The method of claim 1, wherein the test sequence further comprises a preconditioning potential applied prior to the DC block.

14. The method of claim 13, wherein the preconditioning potential comprises a positive DC pulse.

15. The method of claim 13, wherein the preconditioning potential comprises a triangular waveform.

16. The method of claim 1, wherein the analyte concentration is a glucose concentration.

17. The method of claim 1, wherein the test sequence further comprises a second DC block, the second DC block having a waveform distinct from a waveform of the first DC block.

18. The method of claim 17, wherein the second DC waveform has a shape selected from the group consisting of a triangular excitation, sinusoidal excitation and trapezoidal excitation.

19. A method of electrochemically measuring an analyte in a fluid sample, the method comprising the steps of:
applying an electrical test sequence to an electrochemical biosensor, the biosensor comprising:
an electrode system,
a reagent in electrical communication with the electrode system, and
a receptacle configured to contact the fluid sample provided to the biosensor,
with the fluid sample in fluidic contact with the reagent, wherein the test sequence comprises at least one direct current (DC) block configured to produce response information to the test sequence, wherein the DC block includes at least one recovery potential, and wherein a closed circuit condition of the electrode system is maintained during the DC block;
measuring information from the response to the test sequence, including information from the at least one recovery potential; and
determining an analyte concentration of the fluid sample using the information, the determining based at least in part upon the information from the at least one recovery potential.

20. The method of claim 19, wherein the DC block comprises a pulsed sequence of about one pulse to about ten pulses, wherein an excitation pulse is at about +450 mV and the at least one recovery pulse is at about 0 mV, and wherein each pulse is applied for about 50 msec to about 500 msec.

21. The method of claim 20, wherein each excitation pulse at about +450 mV is applied for about 250 msec and each recovery pulse at about 0 mV is applied for about 500 msec, and wherein a ramp rate between the excitation pulse and recovery pulse is controlled to be within a predetermined range, and wherein the ramp rate is from about 10 mV/msec to about 50 mV/msec.

* * * * *